United States Patent
Ueda et al.

(10) Patent No.: US 11,185,293 B2
(45) Date of Patent: Nov. 30, 2021

(54) MEDICAL IMAGE DIAGNOSTIC APPARATUS AND MAGNETIC RESONANCE IMAGING APPARATUS

(71) Applicant: Toshiba Medical Systems Corporation, Otawara-shi (JP)

(72) Inventors: Yu Ueda, Utsunomiya (JP); Hiromitsu Takamori, Yokohama (JP); Takashi Sasaki, Yokohama (JP); Aira Hotta, Kawasaki (JP); Takahiro Murata, Sagamihara (JP)

(73) Assignee: Canon Medical Systems Corporation, Otawara (JP)

( * ) Notice: Subject to any disclaimer, the term of this patent is extended or adjusted under 35 U.S.C. 154(b) by 340 days.

(21) Appl. No.: 15/336,354

(22) Filed: Oct. 27, 2016

(65) Prior Publication Data
US 2017/0119320 A1    May 4, 2017

(30) Foreign Application Priority Data

Oct. 30, 2015  (JP) .............................. JP2015-214741

(51) Int. Cl.
*A61B 5/00*     (2006.01)
*A61B 5/055*    (2006.01)
(Continued)

(52) U.S. Cl.
CPC ............ *A61B 5/7445* (2013.01); *A61B 5/055* (2013.01); *A61B 5/11* (2013.01); *A61B 5/704* (2013.01);
(Continued)

(58) Field of Classification Search
CPC ....... A61B 5/7445; A61B 5/0555; A61B 5/11; A61B 5/704; A61B 5/7405; A61B 5/0042;
(Continued)

(56) References Cited

U.S. PATENT DOCUMENTS 6,414,490 B1 *   7/2002  Damadian .............. A61B 5/055
                                                    324/318
2005/0283068 A1 * 12/2005  Zuccolotto ........... A61B 5/0555
                                                    600/410
(Continued)

FOREIGN PATENT DOCUMENTS

CN      102988044 A     3/2013
CN      204076246 U     1/2015
(Continued)

OTHER PUBLICATIONS

Machine Translation of JP-2000157505-A (Year: 2000).*
(Continued)

*Primary Examiner* — Amelie R Davis
*Assistant Examiner* — John Denny Li
(74) *Attorney, Agent, or Firm* — Oblon, McClelland, Maier & Neustadt, L.L.P.

(57) ABSTRACT

According to one embodiment, a medical image diagnostic apparatus includes a gantry, a couch, a movable base, a screen, a reflecting plate, and a support body. The gantry has a bore formed therein and performs medical imaging. The couch is configured to move the table top along the central axis of the bore. The movable base is provided independently of the table top so as to be movable along the central axis of the bore. The screen is provided on the movable base. An image from a projector is projected on the screen. The reflecting plate reflects the image projected on the screen. The support body is provided on the movable base and supports the reflecting plate.

23 Claims, 19 Drawing Sheets

(51) Int. Cl.
  *A61B 5/11* (2006.01)
  *A61M 21/02* (2006.01)
  *A61M 21/00* (2006.01)
(52) U.S. Cl.
  CPC .......... *A61B 5/7405* (2013.01); *A61M 21/02* (2013.01); *A61B 5/0042* (2013.01); *A61M 2021/005* (2013.01); *A61M 2205/507* (2013.01)
(58) Field of Classification Search
  CPC ............ A61M 21/02; A61M 2021/005; A61M 2205/507; G01R 33/283
  See application file for complete search history.

(56) References Cited

U.S. PATENT DOCUMENTS

| | | | |
|---|---|---|---|
| 2006/0074305 A1 | 4/2006 | Mostafavi | |
| 2006/0079763 A1* | 4/2006 | Jeung | A61B 6/032 600/428 |
| 2013/0218004 A1* | 8/2013 | Yang | G01R 33/283 600/415 |
| 2014/0303477 A1* | 10/2014 | Sunazuka | A61B 5/0555 600/407 |
| 2016/0174914 A1* | 6/2016 | Lerch | A61B 6/0407 5/601 |

FOREIGN PATENT DOCUMENTS

| | | | |
|---|---|---|---|
| JP | 63-102412 U | | 7/1988 |
| JP | H01-166749 A | | 6/1989 |
| JP | H04-303420 A | | 10/1992 |
| JP | H09-28689 A | | 2/1997 |
| JP | H10-66683 A | | 3/1998 |
| JP | 2000157505 A | * | 6/2000 |
| JP | 2001-314391 | | 11/2001 |
| JP | 2003-190112 | | 7/2003 |
| JP | 2013-150702 A | | 8/2013 |
| JP | 2014195616 A | * | 10/2014 |
| JP | 2014-212945 A | | 11/2014 |

OTHER PUBLICATIONS

Machine Translation of JP-2014195616-A (Year: 2014).*
Chinese Office Action dated Jul. 15, 2019, issued in Chinese Patent Application No. 201610969212.X.
Japanese Office Action dated Jul. 2, 2019, issued in Japanese Patent Application No. 2015-214741.
Chinese Office Action dated Feb. 6, 2020, issued in Chinese Patent Application No. 201610969212.X.
Japanese Office Action dated Mar. 9, 2021, issued in Japanese Patent Application No. 2020-039688.

* cited by examiner

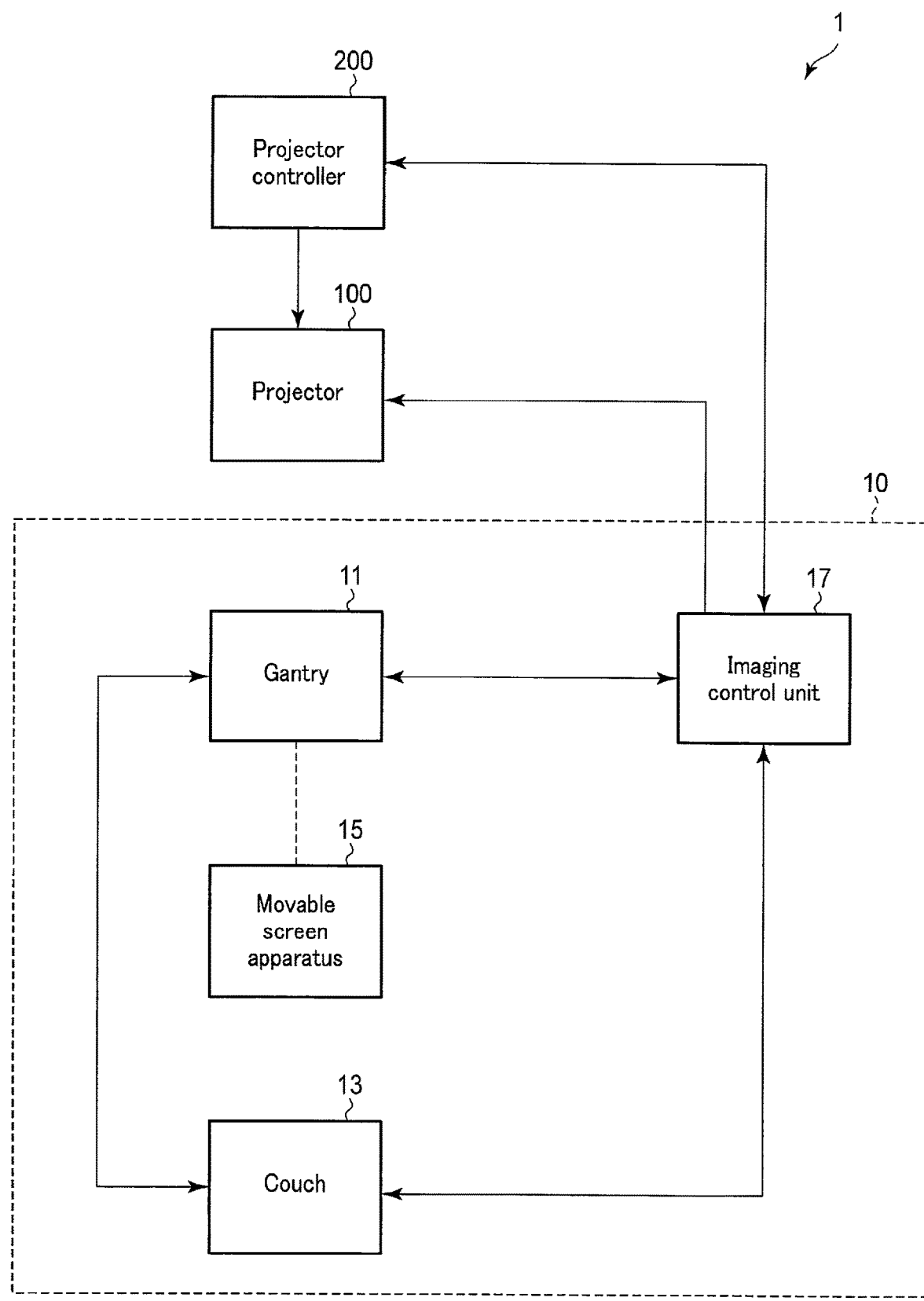
F I G. 1

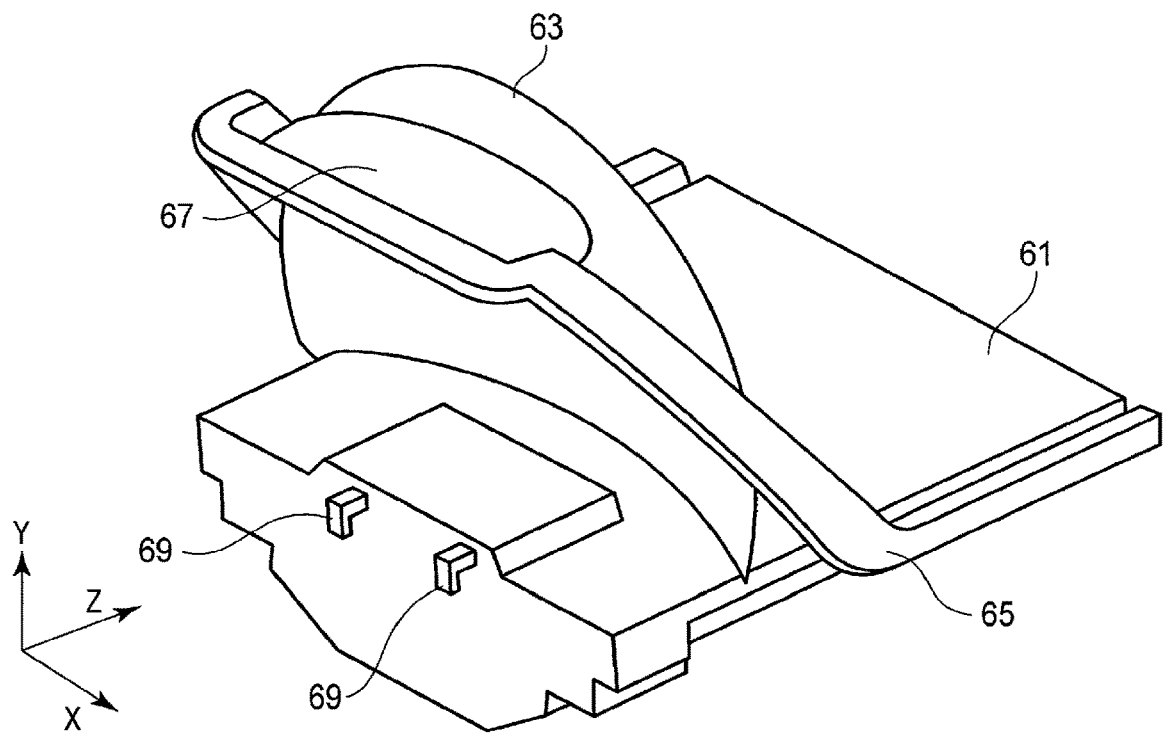
F I G. 5
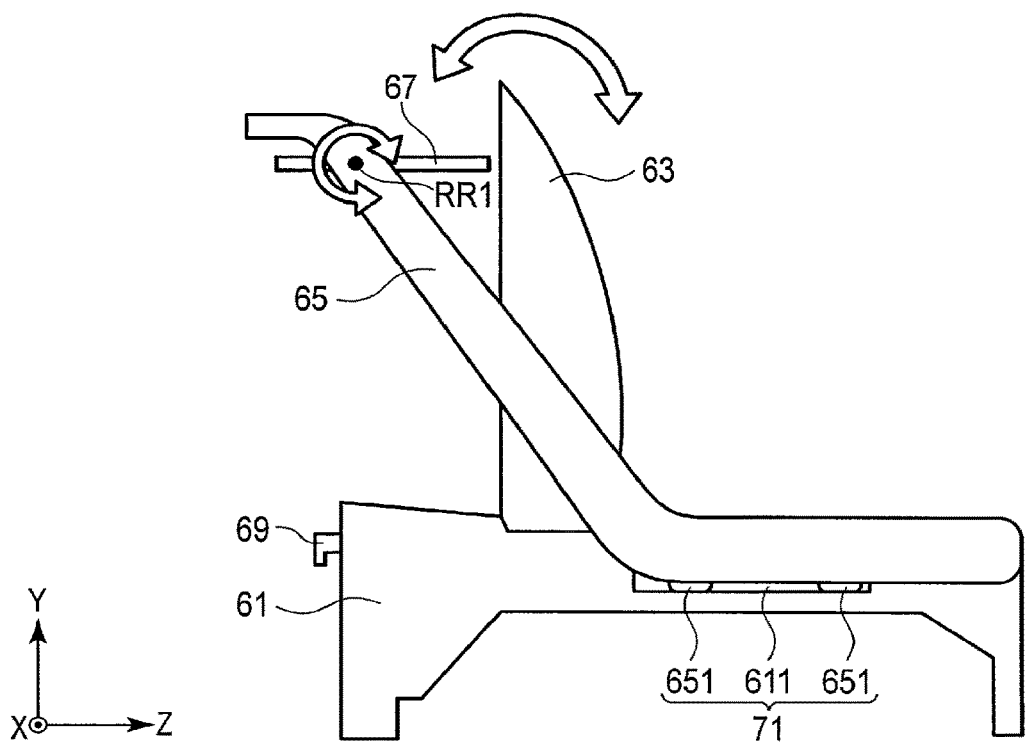
F I G. 6

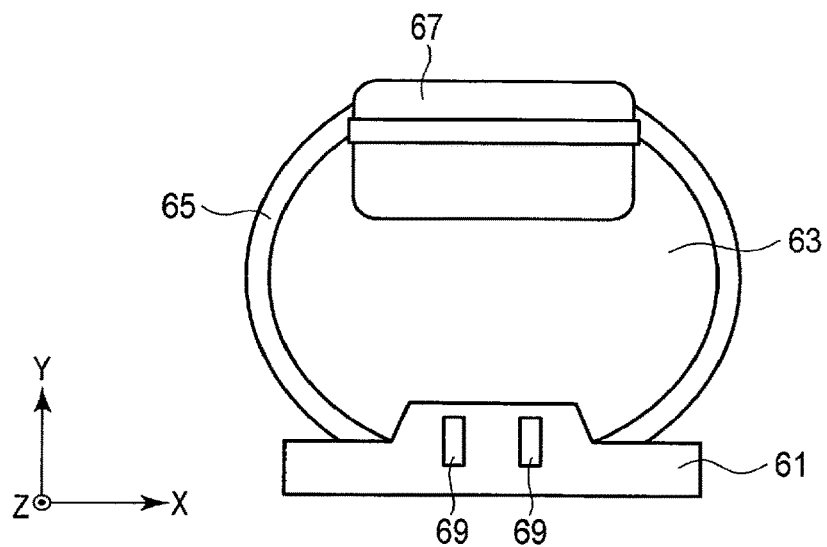
F I G. 7
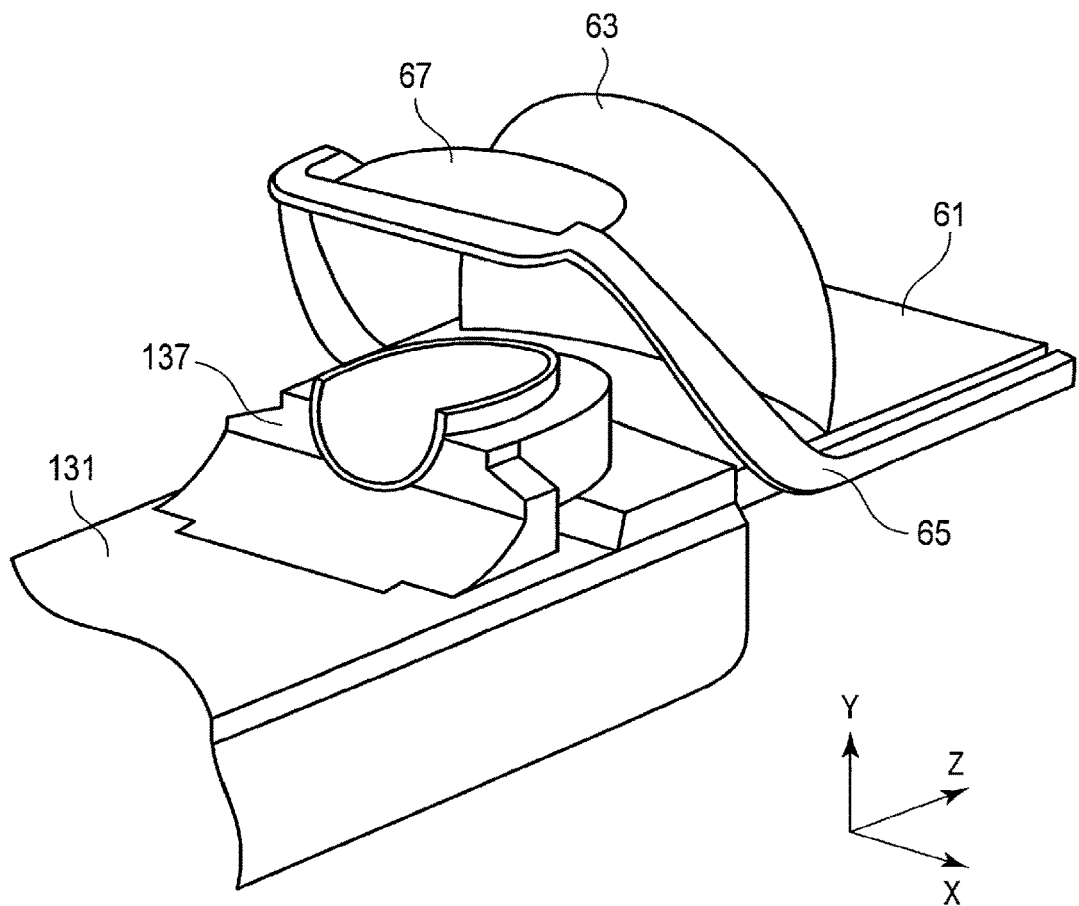
F I G. 8

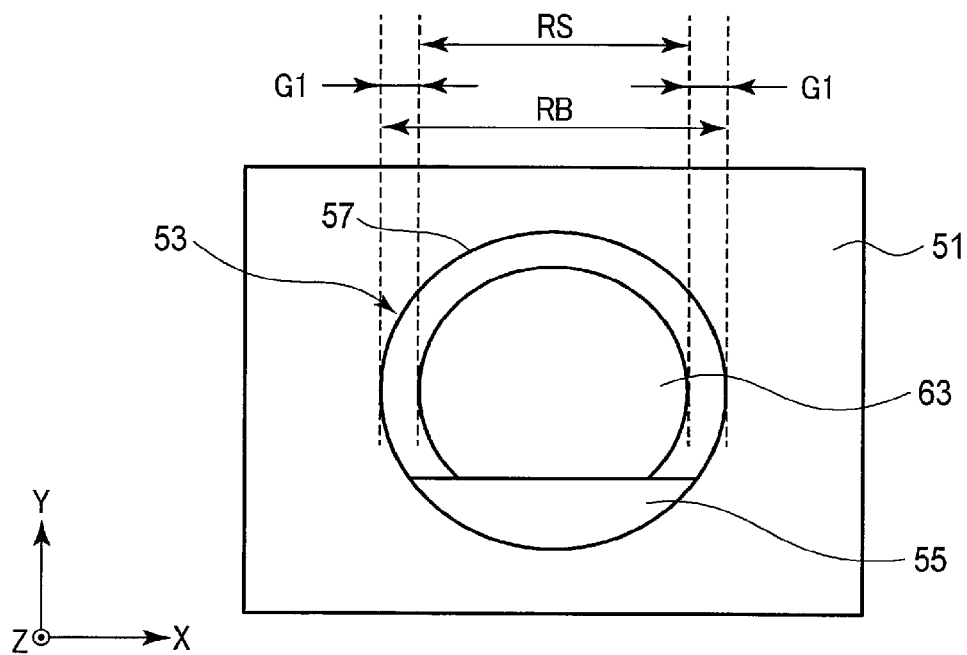
F I G. 9
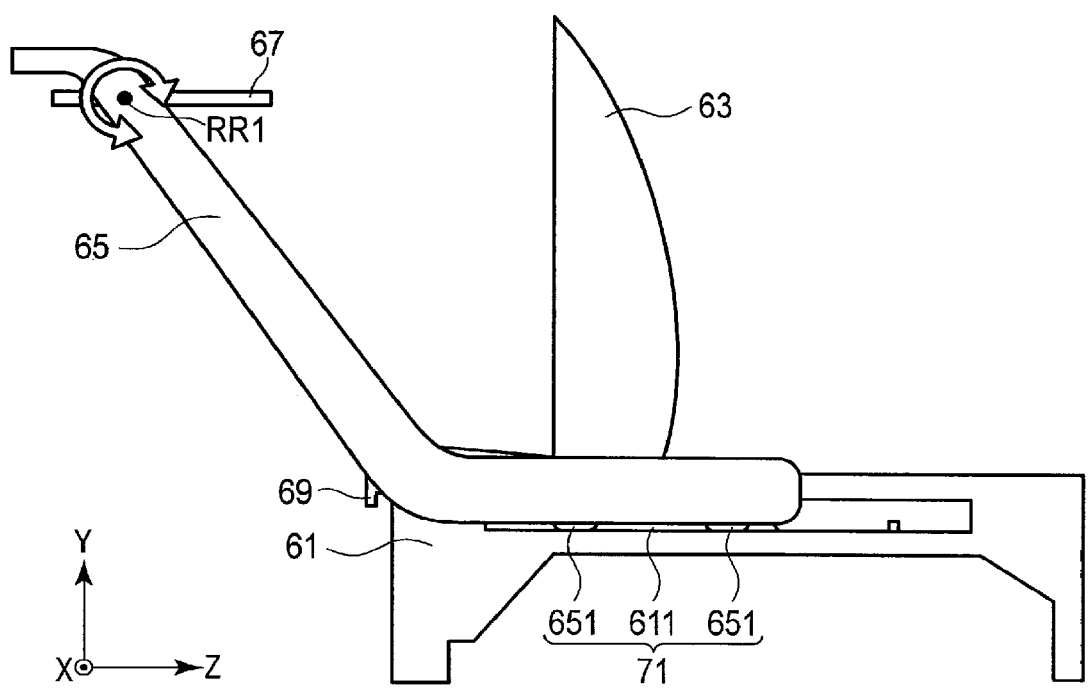
F I G. 10

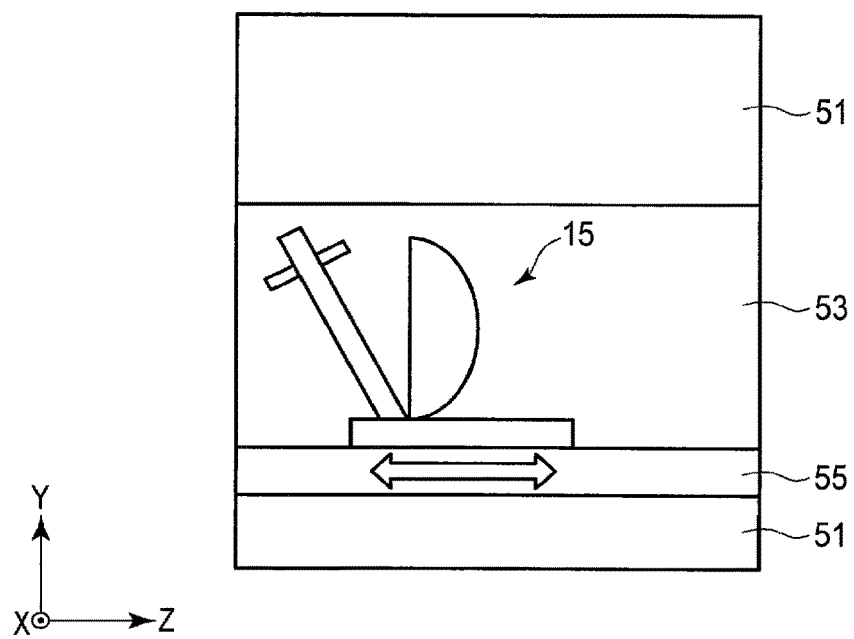
F I G. 11
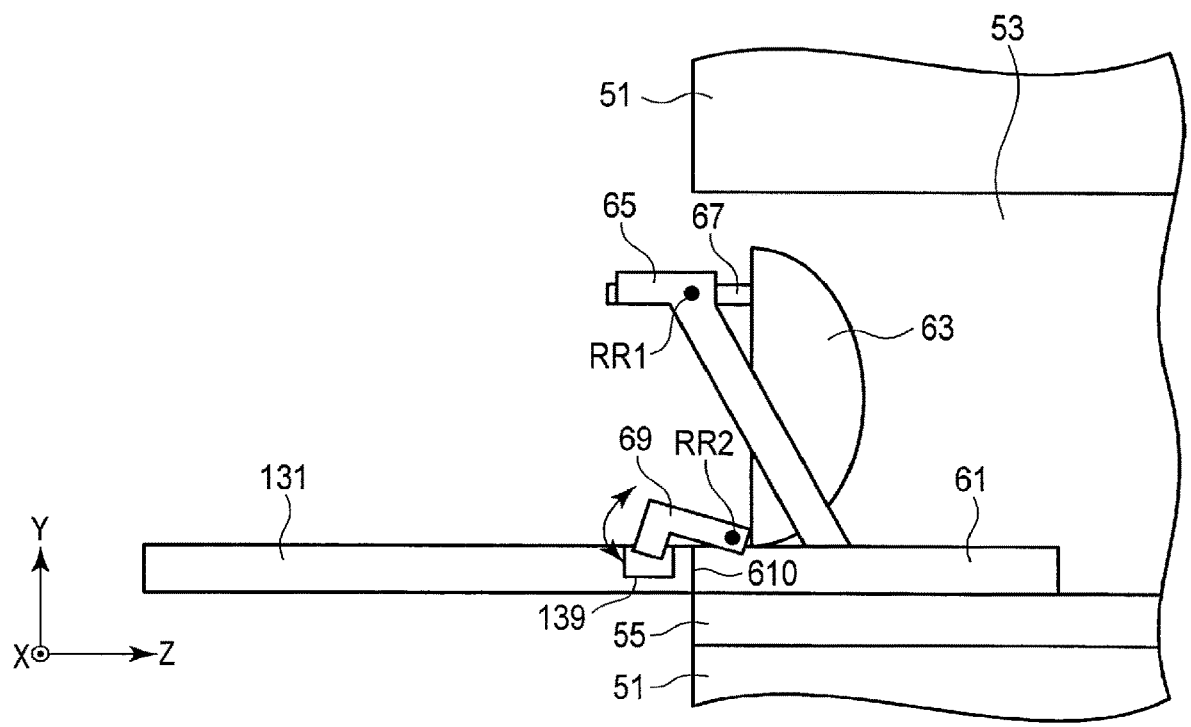
F I G. 12

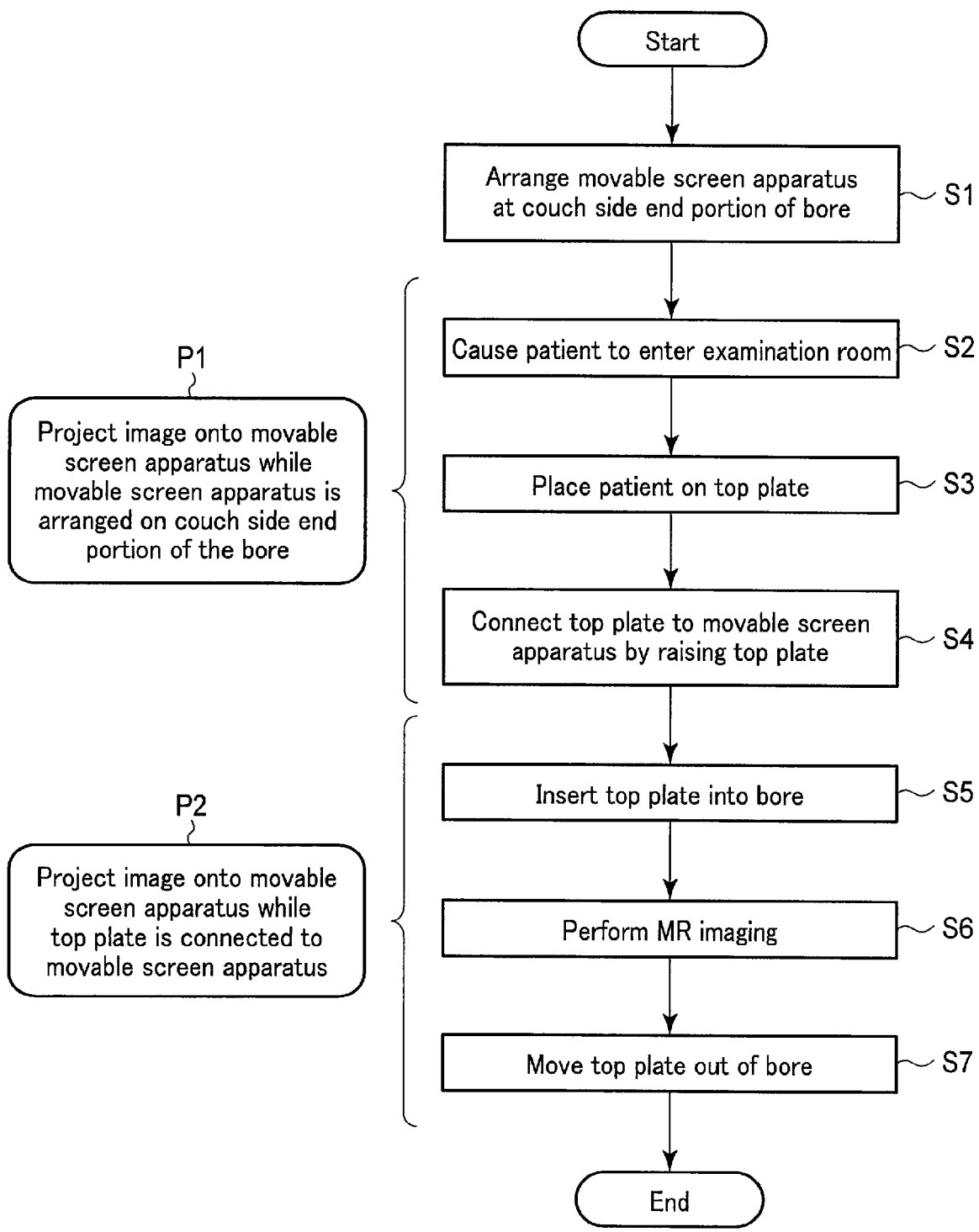
F I G. 15

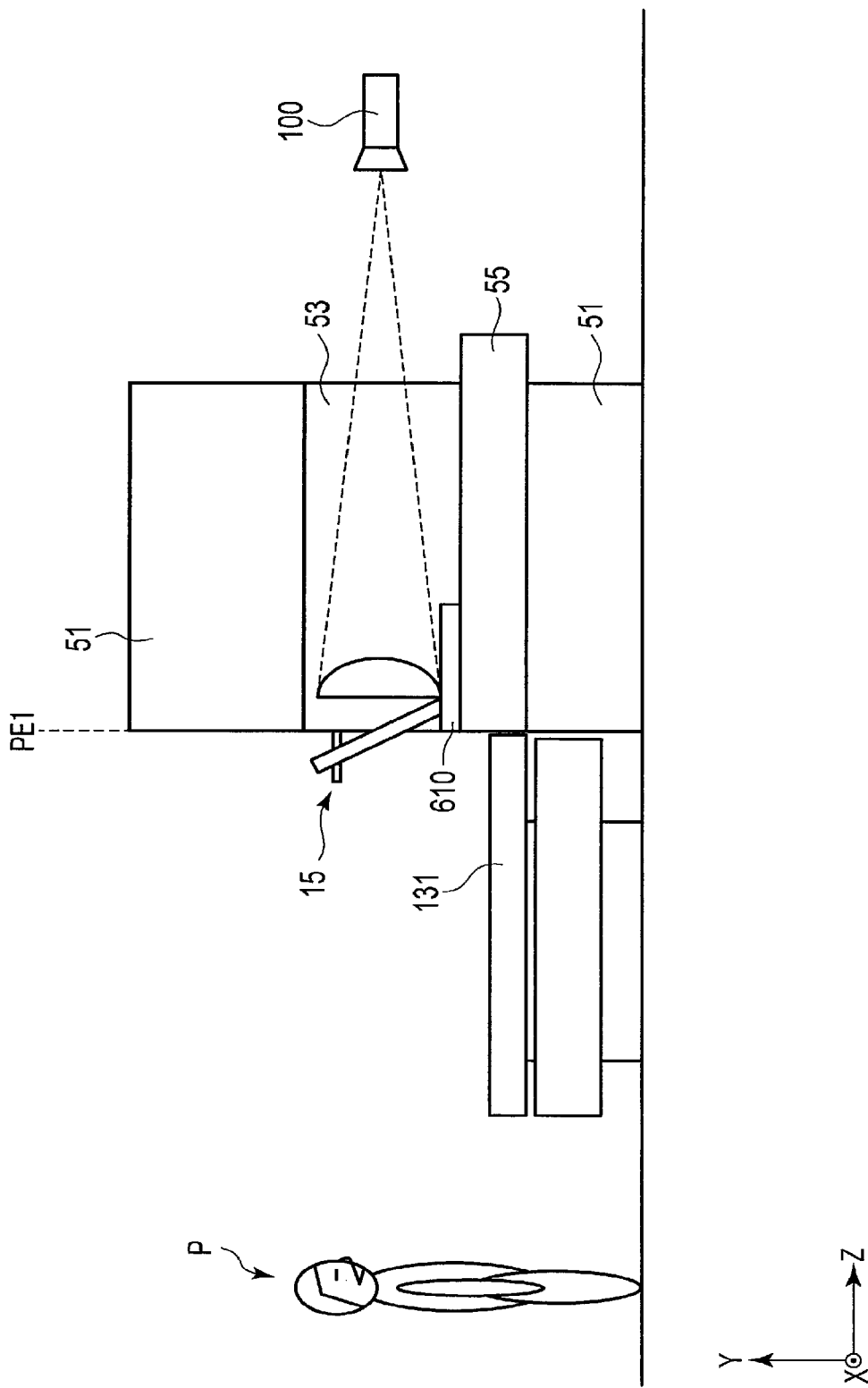
F I G. 16

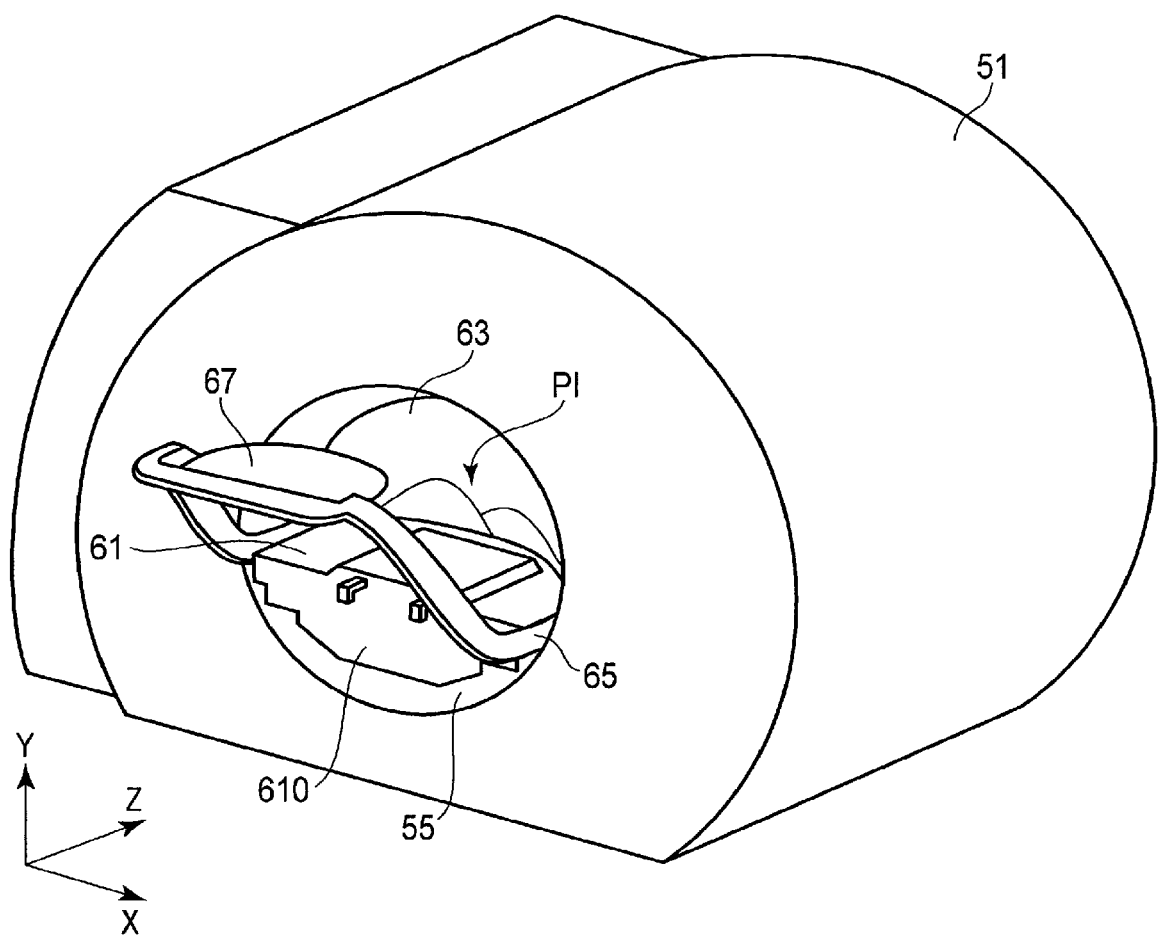
F I G. 17

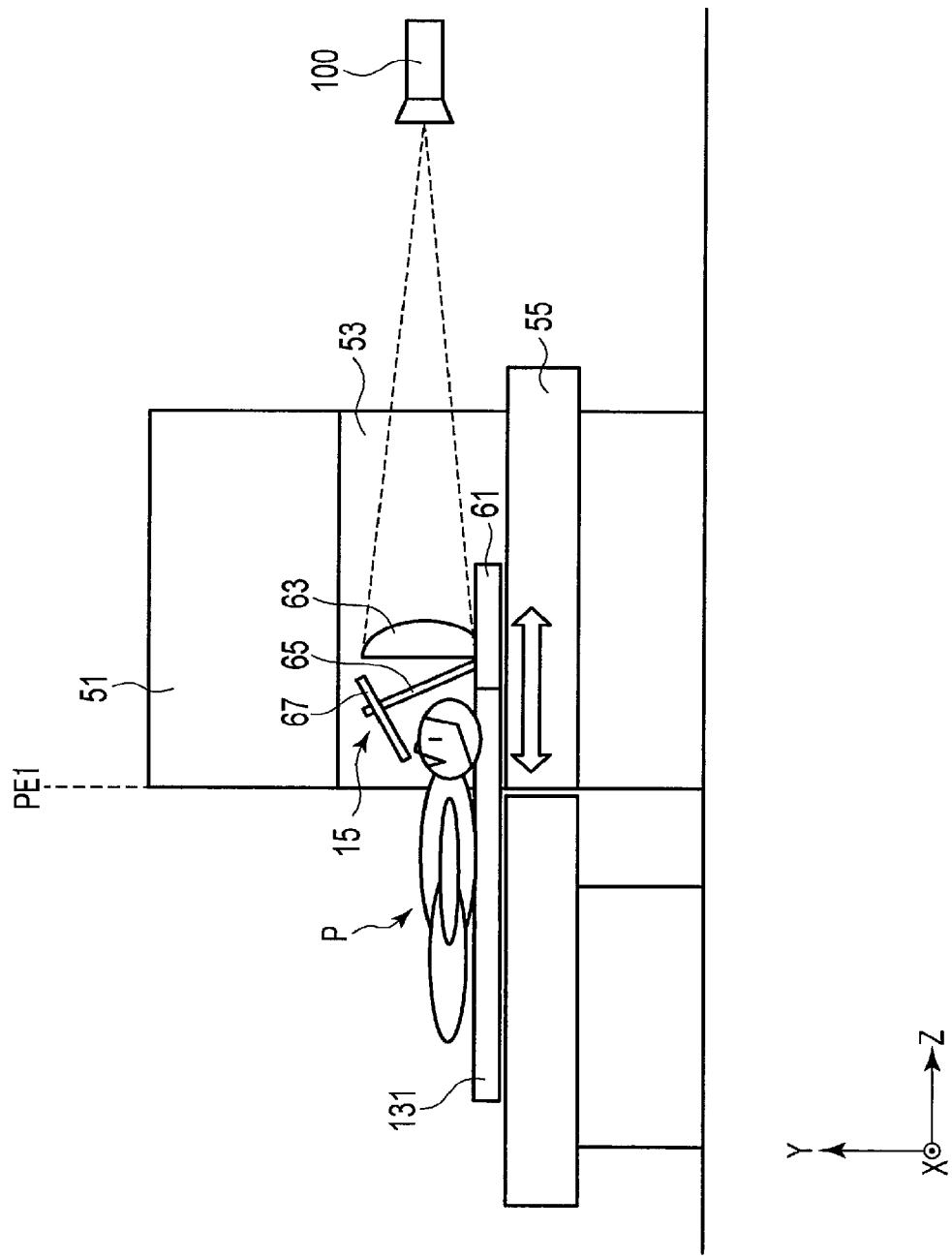
F I G. 18

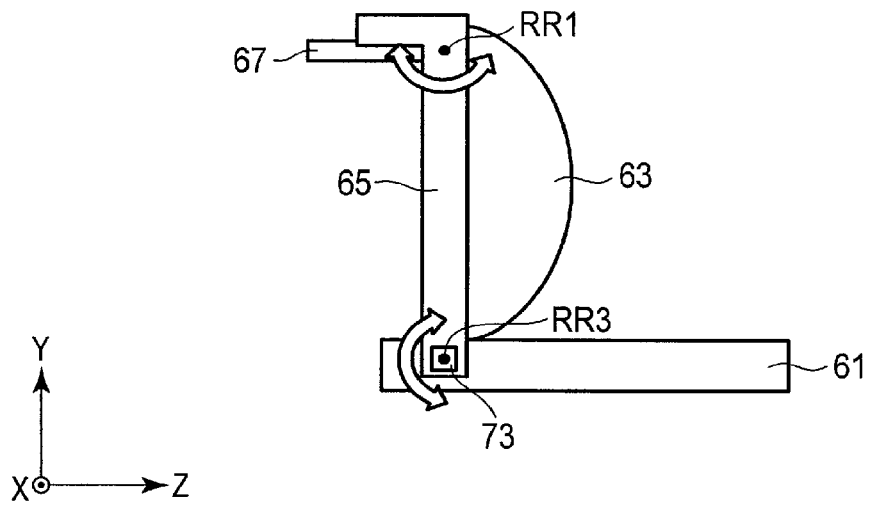
F I G. 19
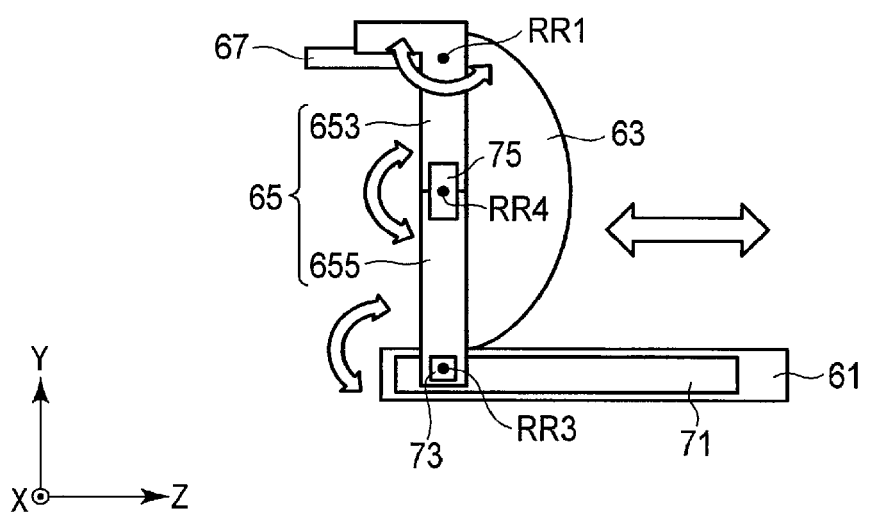
F I G. 20

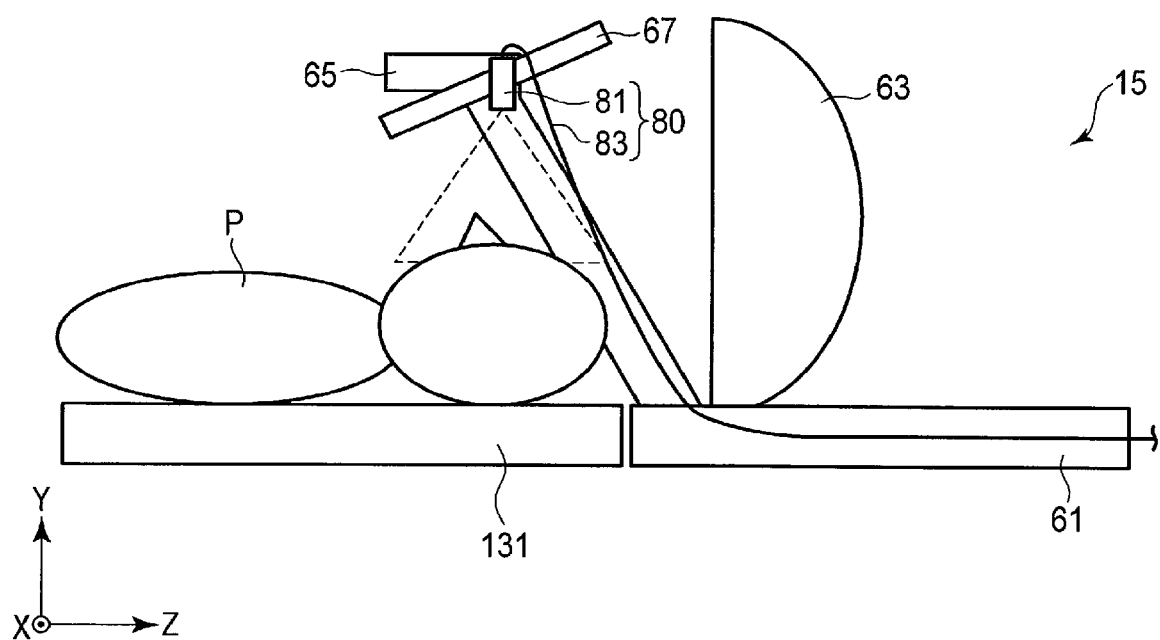
F I G. 21
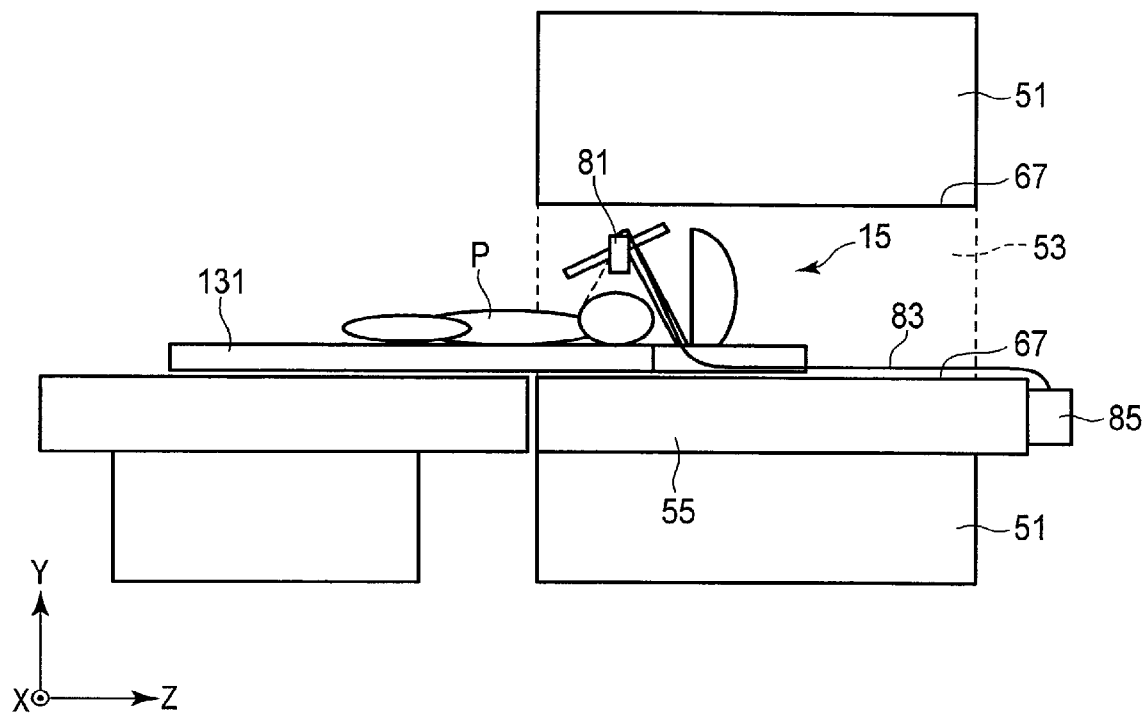
F I G. 22

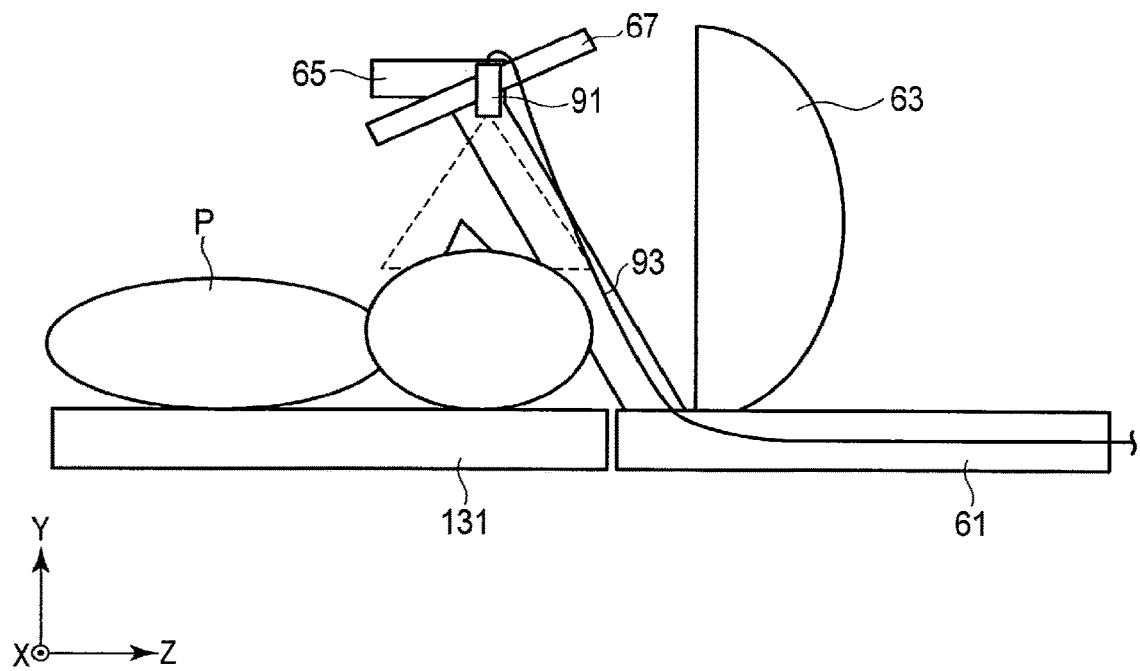
F I G. 25
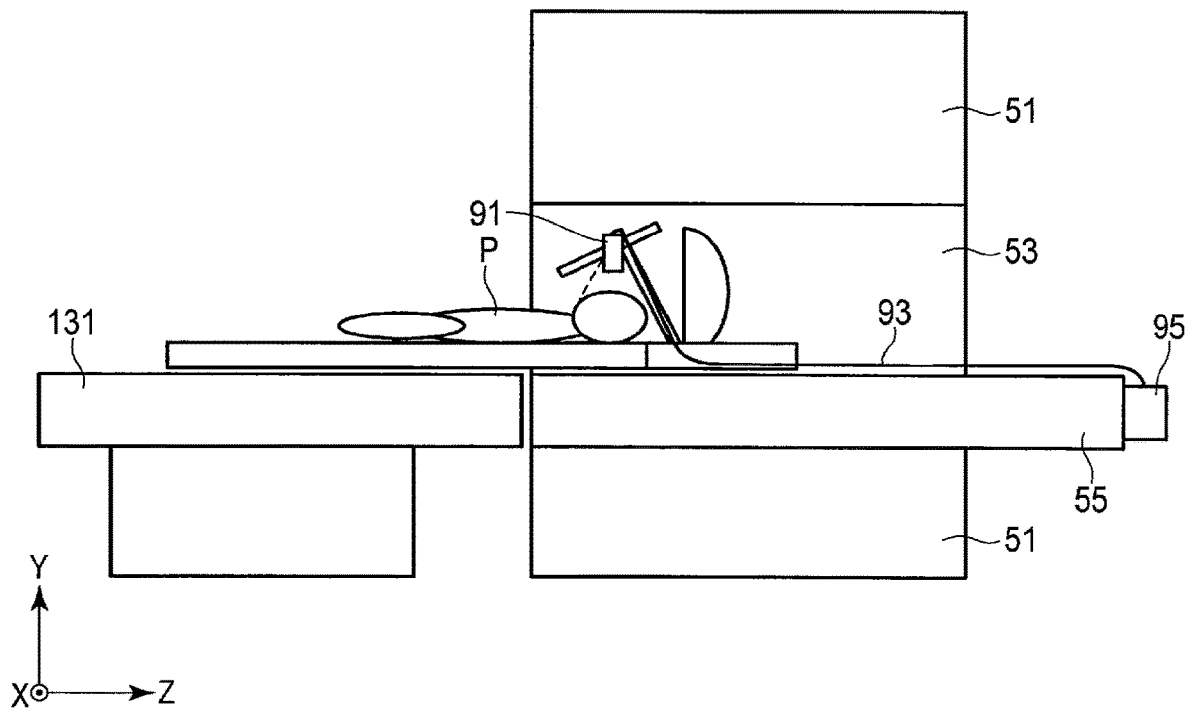
F I G. 26

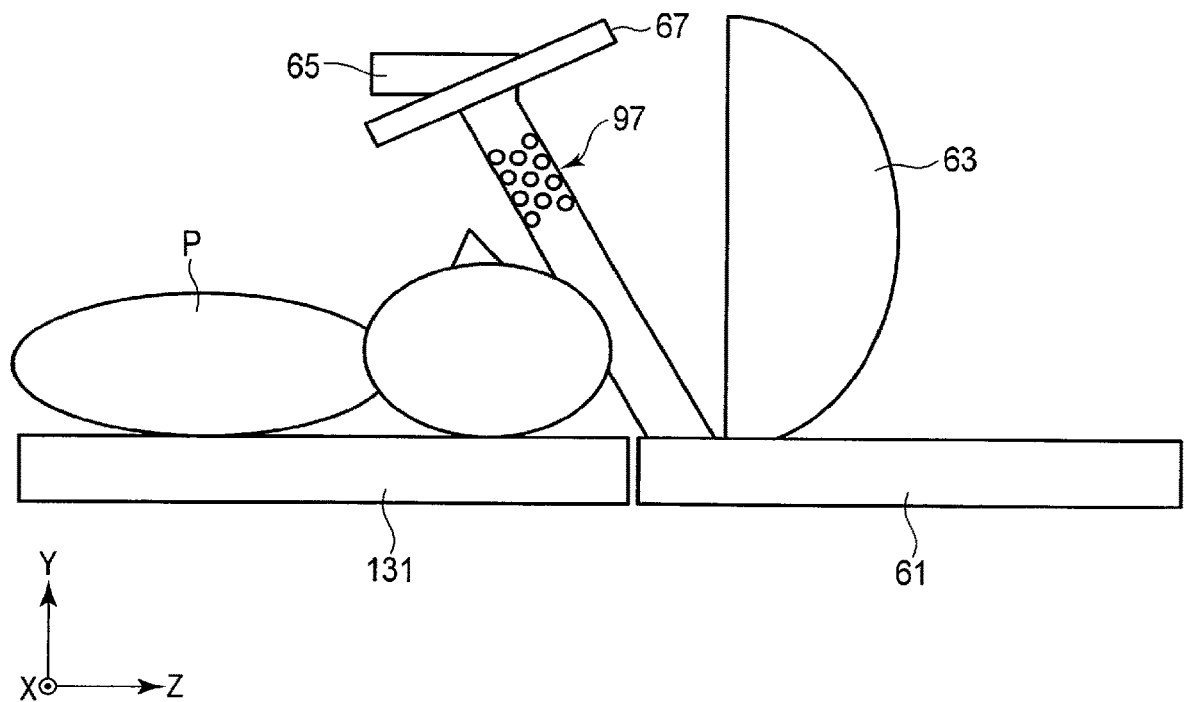
F I G. 27
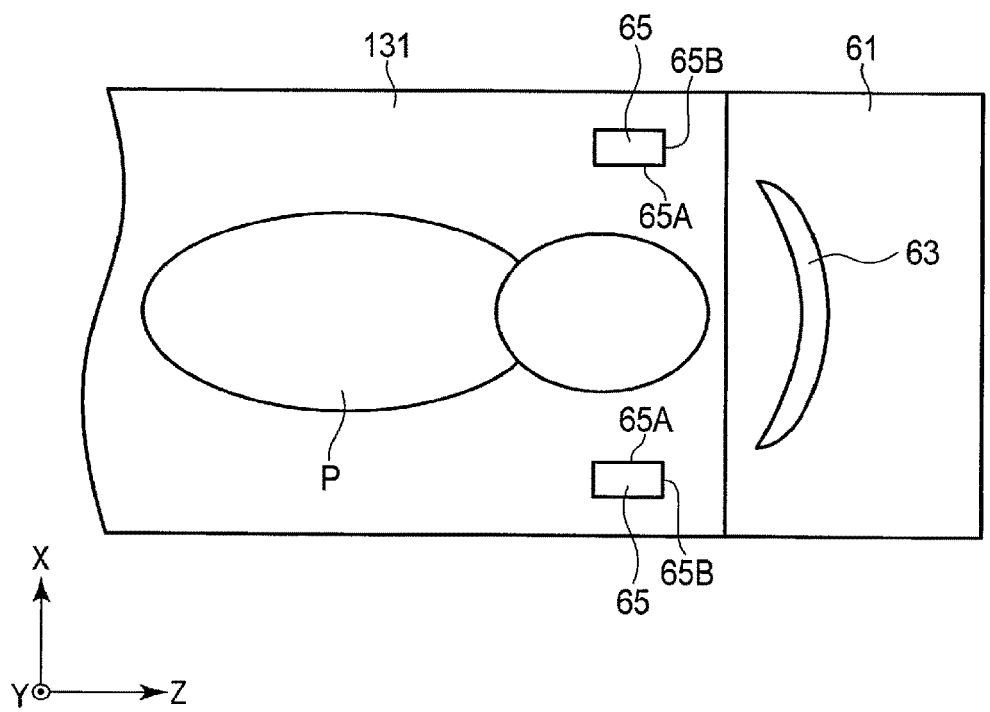
F I G. 28

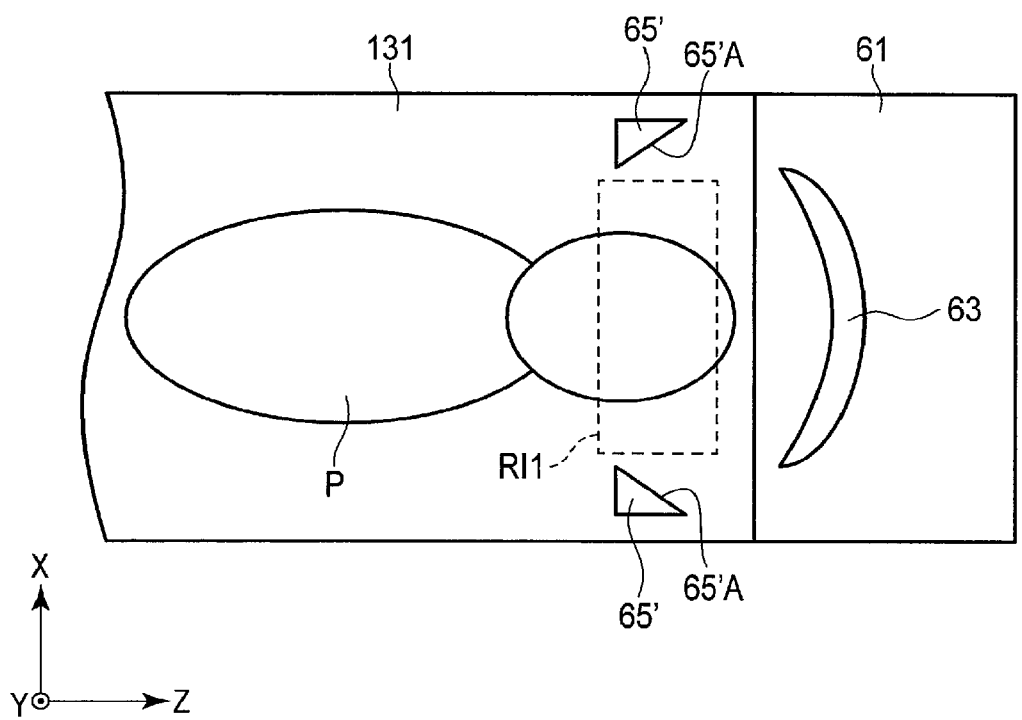
F I G. 29

MEDICAL IMAGE DIAGNOSTIC APPARATUS AND MAGNETIC RESONANCE IMAGING APPARATUS

CROSS-REFERENCE TO RELATED APPLICATIONS

This application is based upon and claims the benefit of priority from the prior Japanese Patent Application No. 2015-214741, filed Oct. 30, 2015 the entire contents of which are incorporated herein by reference.

FIELD

Embodiments described herein relate generally to a medical image diagnostic apparatus and a magnetic resonance imaging apparatus.

BACKGROUND

A magnetic resonance imaging apparatus has a gantry equipped with an imaging mechanism such as a magnet. A bore having an almost hollow shape is formed in the gantry. MR (Magnetic Resonance) imaging is performed while a patient is inserted in the bore. Although gantry having relatively large bore diameters has been developed, MR examinations make not a few patients feel stress because of long MR imaging times, noise during driving of the gantries, and oppressive feelings and feelings of confinement in the bores.

BRIEF DESCRIPTION OF THE DRAWING

FIG. 1 is a block diagram showing the arrangement of a medical image diagnostic system including a medical image diagnostic apparatus according to an embodiment;

FIG. 5 is a perspective view of a movable screen apparatus according to this embodiment;

FIG. 6 is a side view of the movable screen apparatus in FIG. 5;

FIG. 7 is a front view of the movable screen apparatus in FIG. 5;

FIG. 8 is a perspective view of the movable screen apparatus and a table top which are connected to each other according to this embodiment;

FIG. 9 is a schematic front view of a screen arranged in a bore according to this embodiment;

FIG. 10 is a side view of the movable screen apparatus whose support arm in FIG. 6 is slid with respect to the Z-axis;

FIG. 11 is a schematic side view of the movable screen apparatus arranged in the bore of the gantry according to this embodiment;

FIG. 12 is a schematic side view of the movable screen apparatus and the table top according to this embodiment;

FIG. 15 is a flowchart showing a typical procedure for an MR examination using the magnetic resonance imaging system according to this embodiment;

FIG. 16 is a view showing the movable screen apparatus in the first projection mode according to this embodiment when viewed from a side of the gantry;

FIG. 17 is a perspective view showing the movable screen apparatus in the first projection mode according to this embodiment when viewed from the front surface of the gantry;

FIG. 18 is a view showing the movable screen apparatus in the second projection mode according to this embodiment when viewed from a side of the gantry;

FIG. 19 is a view schematically showing a movable screen apparatus according to Application Example 1;

FIG. 20 is a view schematically showing a movable screen apparatus according to Application Example 2;

FIG. 21 is a side view showing a movable screen apparatus according to Application Example 3;

FIG. 22 is an overall side view of the movable screen apparatus and the gantry according to Application Example 3;

FIG. 25 is a side view of a movable screen apparatus according to Application Example 5;

FIG. 26 is an overall side view of the movable screen apparatus and the gantry according to Application Example 5;

FIG. 27 is a side view of a movable screen apparatus according to Application Example 6;

FIG. 28 is a view showing an X-Z section (horizontal section) of the support arm according to this embodiment; and FIG. 29 is a view showing an X-Z section (horizontal section) of a support arm according to Application Example 8.

DETAILED DESCRIPTION

Figure 2:
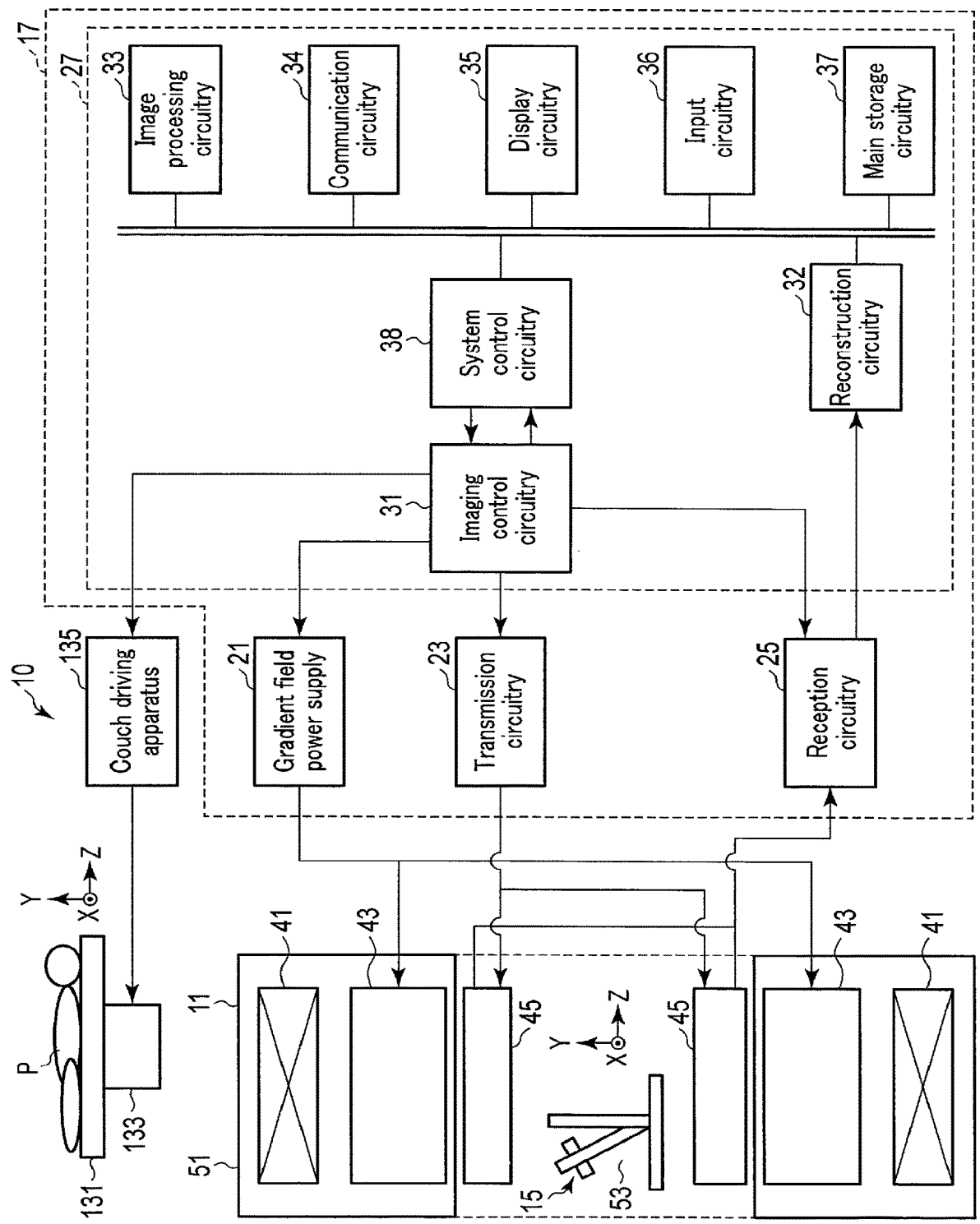
FIG. 2 is a block diagram showing the arrangement of a magnetic resonance imaging apparatus according to this embodiment.

A medical image diagnostic apparatus according to an embodiment includes a gantry, a couch, a movable base, a screen, a reflecting plate, and a support body. The gantry has a bore formed therein and performs medical imaging. The couch is configured to move the table top along the central axis of the bore. The movable base is provided independently of the table top so as to be movable along the central axis of the bore. The screen is provided on the movable base. An image from a projector is projected on the screen. The reflecting plate reflects the image projected on the screen. The support body is provided on the movable base and supports the reflecting plate.

The following techniques can be considered as techniques for reducing stress in MR examinations. For example, there are available: (1) a goggle type head mounted display; (2) the installation of a liquid crystal monitor on the ceiling or wall of an examination room; and (3) a head coil attached with a mirror for seeing an image on a liquid crystal monitor arranged behind the gantry. In the case of technique (1), attaching a head mounted display on the head region of a patient makes the patient feel an oppressive feeling and a feeling of confinement. In the case of technique (2), the patient cannot see any image on the liquid crystal monitor when entering the gantry. In the case of technique (3), since the patient can see an image via the mirror attached to the head coil during MR imaging, the oppressive feeling caused by the bore can be reduced. However, a mirror needs to be attached to each head coil. In addition, since the mirror is attached in a gap with respect to the head coil covering the head region, the patient cannot have much feeling of spread of an image. Furthermore, since the liquid crystal monitor is installed behind the gantry so as not to hide the front of the gantry, the patient can easily visually recognize the bore when he/she is located outside the gantry before MR imaging. Even if, therefore, the patient sees an image via the mirror attached to the head coil thereafter, he/she cannot get rid of a feeling of existing in the bore. In addition, since the positional relationship between the mirror and the liquid crystal monitor changes with the movement of the table top, even if the patient sees an image on the liquid crystal monitor via the mirror during the movement of the table top, he/she keeps having a feeling of moving forward in the bore.

The medical image diagnostic apparatus and the magnetic resonance imaging apparatus according to this embodiment will be described below with reference to the accompanying drawing.

FIG. 1 shows the arrangement of a medical image diagnostic system 1 including a medical image diagnostic apparatus 10 according to this embodiment. As shown in FIG. 1, the medical image diagnostic system 1 includes the medical image diagnostic apparatus 10, a projector 100, and a projector controller 200 which are communicably connected to each other wiredly or wirelessly. The medical image diagnostic apparatus 10 includes a gantry 11, a couch 13, a movable screen apparatus 15, and an imaging control unit 17. For example, the gantry 11, the couch 13, and the movable screen apparatus 15 are installed in an examination room. The imaging control unit 17 is installed in a control room adjacent to the examination room. The gantry 11 is equipped with a mechanism for implementing medical imaging. A bore having a hollow shape is formed in the gantry 11. The couch 13 is installed in front of the gantry 11. The couch 13 movably supports the table top on which a patient P is placed. The couch 13 moves the table top under the control of the gantry 11, a console, and the like. The movable screen apparatus 15 is movably provided in the bore of the gantry 11. The projector 100 is installed in the front or back of the gantry 11. An image from the projector 100 is projected on the movable screen apparatus 15.

The projector controller 200 is a computer apparatus which controls the projector 100. The projector controller 200 supplies data concerning an image of a projection target to the projector 100. The projector 100 projects an image corresponding to data from the projector controller 200 onto the screen of the movable screen apparatus 15. The projector 100 may use, for example, a liquid crystal system, DLP (Digital Light Processing) system, LCOS (Liquid Crystal On Silicon) system, or GLV (Grating Light Valve) system. In this case, the projector 100 is equipped with at least a display device and a light source. The display device displays an image corresponding to data from the projector controller 200. The light source irradiates the display device with light directly or indirectly through an optical system. Light (to be referred to as projection light hereinafter) transmitted through or reflected by the display device emerges to the outside of the projector 100 directly or indirectly through an optical system. Irradiating the movable screen apparatus 15 with projection light will project an image corresponding to the projection light onto the movable screen apparatus 15.

The imaging control unit 17 functions as the main unit of the medical image diagnostic apparatus 10. For example, the imaging control unit 17 controls the gantry 11 to perform medical imaging. In addition, the imaging control unit 17 reconstructs a medical image concerning the patient P based on raw data acquired by the gantry 11 in medical imaging. Note that the imaging control unit 17 may be configured to control the projector 100 via the projector controller 200. In addition, the imaging control unit 17 may supply data concerning an image of a projection target to the projector 100. In this case, the projector 100 projects an image corresponding to data from the imaging control unit 17 onto the screen of the movable screen apparatus 15.

Note that the arrangement of the medical image diagnostic system 1 according to this embodiment is not limited to only the above arrangement. For example, if the imaging control unit 17 has a function of controlling the projector 100 by using the projector controller 200 described above, the projector controller 200 need not be provided for the medical image diagnostic system 1.

The medical image diagnostic system 1 according to this embodiment can improve the interior comfortability in the bore at the time of medical imaging using the medical image diagnostic apparatus 10 by using the projector 100 and the movable screen apparatus 15. The medical image diagnostic apparatus 10 according to this embodiment may be any apparatus which can obtain an image of the patient P by using the gantry 11 in which a bore is formed. More specifically, as the medical image diagnostic apparatus 10 according to this embodiment, it is possible to use a single modality such as an MRI (Magnetic Resonance Imaging) apparatus, X-ray CT (Computed Tomography) apparatus, PET (Positron Emission Tomography) apparatus, or SPECT (Single Photon Emission Computed Tomography) apparatus. Alternatively, as the medical image diagnostic apparatus 10 according to the embodiment, it is possible to use a composite modality such as an MR/PET apparatus, CT/PET apparatus, MR/SPECT apparatus, or CT/SPECT apparatus. For the sake of a concrete description, assume that the medical image diagnostic apparatus 10 according to the embodiment is the magnetic resonance imaging apparatus 10. In addition, the medical image diagnostic system 1 including the magnetic resonance imaging apparatus 10, the projector 100, and the projector controller 200 is called the magnetic resonance imaging system 1.

FIG. 2 shows the arrangement of the magnetic resonance imaging apparatus 10 according to this embodiment. As shown in FIG. 2, the magnetic resonance imaging apparatus 10 includes the imaging control unit 17, the gantry 11, the couch 13, and the movable screen apparatus 15. The imaging control unit 17 includes a gradient field power supply 21, transmission circuitry 23, reception circuitry 25, and a console 27. The console 27 includes imaging control circuitry 31, reconstruction circuitry 32, image processing circuitry 33, communication circuitry 34, display circuitry 35, input circuitry 36, main storage circuitry 37, and system control circuitry 38. The imaging control circuitry 31, the reconstruction circuitry 32, the image processing circuitry 33, the communication circuitry 34, the display circuitry 35, the input circuitry 36, the main storage circuitry 37, and the system control circuitry 38 are communicably connected to each other via a bus. The gradient field power supply 21, the transmission circuitry 23, and the reception circuitry 25 are provided independently of the console 27 and the gantry 11.

The gantry 11 includes a static field magnet 41, a gradient field coil 43, and an RF coil 45. In addition, the static field magnet 41 and the gradient field coil 43 are housed in a housing (to be referred to as a gantry housing hereinafter) 51 of the gantry 11. A bore 53 having a hollow shape is formed in the gantry housing 51. The RF coil 45 is arranged in the bore 53 of the gantry housing 51. In addition, the movable screen apparatus 15 according to the embodiment is arranged in the bore 53 of the gantry housing 51.

The static field magnet 41 has a hollow, almost cylindrical shape and generates a static field in the almost cylindrical space. As the static field magnet 41, for example, a permanent magnet, superconducting magnet, or normal conducting magnet is used. In this case, the central axis of the static field magnet 41 is defined as the Z-axis, an axis vertically orthogonal to the Z-axis will be referred to as the Y-axis, and an axis horizontally orthogonal to the Z-axis will be referred to as the X-axis. The X-axis, the Y-axis, and the Z-axis constitute an orthogonal three-dimensional coordinate system.

The gradient field coil 43 is a coil unit which is attached to the inside of the static field magnet 41 and formed into a hollow, almost cylindrical shape. The gradient field coil 43 generates a gradient field upon reception of a current supplied from the gradient field power supply 21.

The gradient field power supply 21 supplies a current to the gradient field coil 43 under the control of the imaging control circuitry 31. The gradient field power supply 21 supplies a current to the gradient field coil 43 to cause it to generate a gradient field.

The RF coil 45 is arranged inside the gradient field coil 43, and generates a high-frequency magnetic field upon reception of an RF pulse from the transmission circuitry 23. In addition, the RF coil 45 receives a magnetic resonance signal (to be referred to as an MR signal hereinafter) generated from a target atomic nucleus existing in the patient P under the action of a high-frequency magnetic field. The received MR signal is supplied to the reception circuitry 25 wiredly or wirelessly. Although the RF coil 45 is described as a coil having a transmission/reception function, a transmission RF coil and a reception RF coil may be separately provided.

The transmission circuitry 23 transmits a high-frequency magnetic field for exciting a target atomic nucleus existing in the patient P to the patient P via the RF coil 45. Typically, as a target atomic nucleus, a proton is used. More specifically, the transmission circuitry 23 supplies a high-frequency signal (RF signal) for exciting a target atomic nucleus to the RF coil 45 under the control of the imaging control circuitry 31. The high-frequency magnetic field generated from the RF coil 45 vibrates at a resonance frequency unique to the target atomic nucleus to excite the target atomic nucleus. An MR signal is generated from the excited target atomic nucleus and detected by the RF coil 45. The detected MR signal is supplied to the reception circuitry 25.

The reception circuitry 25 receives an MR signal generated from an excited target atomic nucleus via the RF coil 45. The reception circuitry 25 generates a digital MR signal by processing the received MR signal. The digital MR signal is supplied to the reconstruction circuitry 32 wiredly or wirelessly.

The couch 13 is arranged adjacent to the gantry 11. The couch 13 includes a table top 131 and a base 133. The patient P is placed on the table top 131. The base 133 supports the table top 131 so as to allow it to slide along the X-axis, the Y-axis, and the Z-axis. The base 133 accommodates a couch driving apparatus 135. The couch driving apparatus 135 moves the table top 131 under the control of the imaging control circuitry 31. As the couch driving apparatus 135, for example, any type of motor such as a servo motor or stepping motor may be used.

The imaging control circuitry 31 includes, as hardware resources, a processor such as a CPU (Central Processing Unit) or MPU (Micro Processing Unit) and a memory such as a ROM (Read Only Memory) or RAM (Random Access Memory). The imaging control circuitry 31 synchronously controls the gradient field power supply 21, the transmission circuitry 23, and the reception circuitry 25 based on pulse sequence information supplied from the system control circuitry 38, and obtains an image of the patient P in accordance with a pulse sequence corresponding to the pulse sequence information.

The reconstruction circuitry 32 includes, as hardware resources, a processor such as a CPU, GPU (Graphical Processing Unit), or MPU and memories such as a ROM and a RAM. The reconstruction circuitry 32 reconstructs an MR image concerning the patient P based on an MR signal from the reception circuitry 25. For example, the reconstruction circuitry 32 generates an MR image defined in a real space by applying Fourier transformation to an MR signal arranged in a k-space or high-frequency space. Note that the reconstruction circuitry 32 may be implemented by an ASIC (Application Specific Integrated Circuit), FPGA (Field Programmable Gate Array), CPLD (Complex Programmable Logic Device), or SPLD (Simple Programmable Logic Device), which implements a reconstruction function.

The image processing circuitry 33 includes, as hardware resources, a processor such as a CPU, GPU, or MPU and memories such as a ROM and a RAM. The image processing circuitry 33 performs various types of image processing for an MR image reconstructed by the reconstruction circuitry 32. Note that the image processing circuitry 33 may be implemented by an ASIC, FPGA, CPLD, or SPLD, which implements the above image processing function.

The communication circuitry 34 performs data communication with the projector controller 200 or the projector 100 wiredly or wirelessly (not shown). In addition, the communication circuitry 34 may perform data communication with an external apparatus such as a PACS server via a network (not shown). The communication circuitry 34 may also perform data communication with a device (to be described later) attached to the movable screen apparatus 15.

The display circuitry 35 displays various types of information. For example, the display circuitry 35 displays an MR image reconstructed by the reconstruction circuitry 32 or an MR image processed by the image processing circuitry 33. The display circuitry 35 may also display an image projected by the projector 100. More specifically, the display circuitry 35 includes display interface circuitry and a display device. The display interface circuitry converts data representing a display target into a video signal. A display signal is supplied to the display device. The display device displays the video signal representing the display target. As the display device, it is possible to use, for example, a CRT display, liquid crystal display, organic EL display, LED display, or plasma display, or another arbitrary type of display known in this technical field as needed.

More specifically, the input circuitry 36 includes an input device and input interface circuitry. The input device accepts various types of commands from the user. As the input device, a keyboard, a mouse, various types of switches, and the like can be used. The input interface circuitry supplies an output signal from the input device to the system control circuitry 38 via a bus. Note that the input circuitry 36 is not limited to circuitry including physical operation components such as a mouse and a keyboard. For example, the input circuitry 36 includes electrical signal processing circuitry which receives an electrical signal corresponding to an input operation from an external input device provided separately from the magnetic resonance imaging apparatus 10 and outputs the received electrical signal to various types of circuits.

The main storage circuitry 37 is a storage device such as an HDD (Hard Disk Drive), SSD (Solid State Drive), or integrated circuit storage device, which stores various types of information. In addition, the main storage circuitry 37 may be, for example, a CD-ROM drive, a DVD drive, or a driving device which reads and writes various types of information from and on a portable storage medium such as a flash memory. For example, the main storage circuitry 37 stores MR images, control programs for the magnetic resonance imaging apparatus 10, and the like.

The system control circuitry 38 includes, as hardware resources, a processor such as a CPU or MPU and memories such as a ROM and a RAM. The system control circuitry 38 functions as the main unit of the magnetic resonance imaging apparatus 10. More specifically, the system control circuitry 38 reads out a control program stored in the main storage circuitry 37 and loads the program in the memory. The system control circuitry 38 then controls each unit of the magnetic resonance imaging apparatus 10 in accordance with the loaded control program.

The magnetic resonance imaging apparatus 10 according to this embodiment will be described in detail below.

Figure 3:
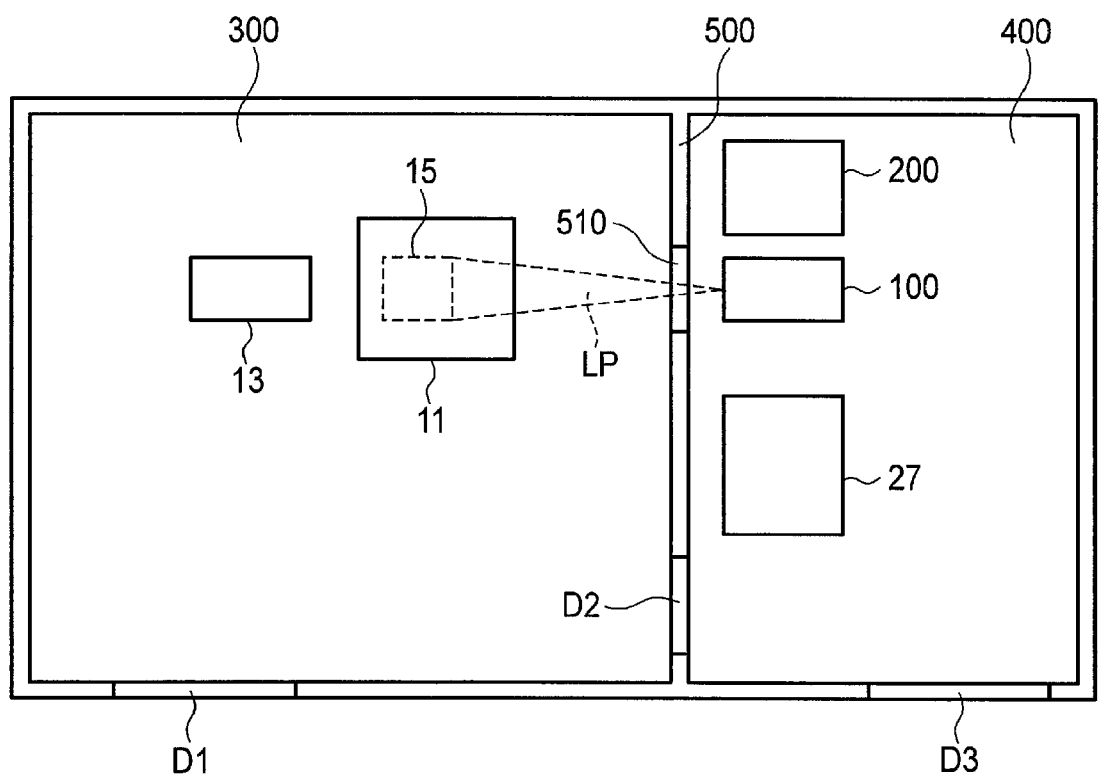
FIG. 3 is a view showing an example of the installation environment of a magnetic resonance imaging system according to this embodiment.

The installation environment of the magnetic resonance imaging system 1 according to this embodiment will be described first with reference to FIG. 3. FIG. 3 shows an example of the installation environment of the magnetic resonance imaging system according to the embodiment. As shown in FIG. 3, an examination room 300 in which MR imaging is performed is provided, together with a control room 400 adjacent to the examination room 300. The gantry 11 and the couch 13 are installed in the examination room 300. The couch 13 is provided in front of the gantry 11. The movable screen apparatus 15 is provided in the bore of the gantry 11. The examination room 300 is a shield room which can shield against leakage magnetic fields from the gantry 11, external electromagnetic fields, and the like. The examination room 300 is provided with a door D1 for entrance and exit. A door D2 for passage between the examination room 300 and the control room 400 is provided between the examination room 300 and the control room 400. The console 27, the projector 100, and the projector controller 200 are installed in the control room 400. The projector 100 is installed behind the gantry 11 on one side of a wall 500 between the examination room 300 and the control room 400. A portion of the wall 500 through which projection light LP propagating from the projector 100 to the movable screen apparatus 15 propagates is provided with a window 510 which can transmit the projection light LP. It is possible to make the projection light LP propagate from the projector 100 installed in the control room 400 to the movable screen apparatus 15 in the examination room 300 via the window 510. The control room 400 is also preferably provided with a door D3 for entrance and exit.

Note that the above layout is an example and is not exhaustive. For example, the projector 100, the projector controller 200, and the console 27 are installed in the control room 400. However, the console 27 and the projector controller 200 may be installed in a room different from that of the projector 100. In addition, the projector 100 may be provided in the examination room 300 as long as the projector 100 is formed from a material which is not affected by a magnetic field. Furthermore, a machine room for the installation of the gradient field power supply 21 and the reception circuitry 25 and the like may be provided in addition to the examination room 300 and the control room 400.

Figure 4:
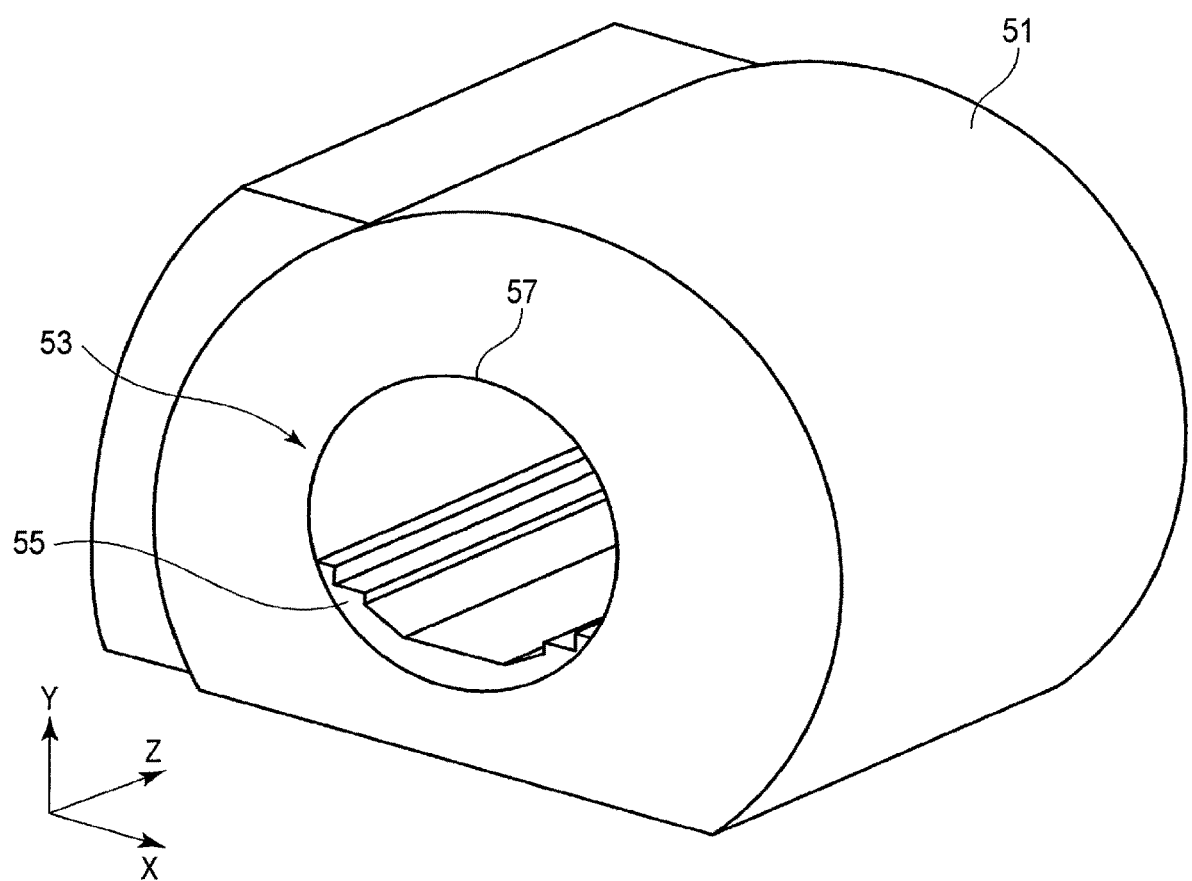
FIG. 4 is a perspective view of a gantry housing according to this embodiment.

An outer appearance of the gantry 11 will be described next with reference to FIG. 4. FIG. 4 is a perspective view of the gantry housing 51 according to this embodiment. As shown in FIG. 4, the bore 53 having a hollow shape is formed in the gantry housing 51. A rail 55 parallel to the central axis Z of the bore 53 is formed on a lower portion of the bore 53 of the gantry housing 51. The rail 55 is a structure which guides a slide along the central axis Z of the table top 131 and the movable screen apparatus 15. The rail 55 is provided on an inner wall 57 of the gantry housing 51 in contact with the bore 53. The rail 55 is formed from a nonmagnetic material having no influence on a magnetic field used for magnetic resonance imaging. In this case, a direction extending from the couch side to the projector side with reference to the Z-axis is defined as a +Z-axis direction, and a direction extending from the projector side to the couch side is defined as a −Z-axis direction.

The structure of the movable screen apparatus 15 will be described next with reference to FIGS. 5, 6, 7, and 8. FIG. 5 is a perspective view of the movable screen apparatus 15 according to this embodiment. FIG. 6 is a side view of the movable screen apparatus 15. FIG. 7 is a front view of the movable screen apparatus 15. FIG. 8 is a perspective view of the movable screen apparatus 15 and the table top 131 which are connected to each other.

As shown in FIGS. 5, 6, 7, and 8, the movable screen apparatus 15 includes a movable carriage 61, a screen 63, a support arm 65, and a reflecting plate 67. The movable carriage 61 is a structure which moves along the rail 55 provided on the inner wall 57 of the gantry housing 51. Wheels (not shown) which roll on the rail 55 are attached to a lower portion of the movable carriage 61. Note that if the movable carriage 61 can move on the rail 55, wheels need not always be provided, and a surface of the movable carriage 61 which comes into contact with the rail 55 may be formed from a material having a low friction coefficient. The movable carriage 61 and the rail 55 are formed to allow the movable carriage 61 to move from an end portion of the bore 53 which is located on the couch 13 side (−Z side) to an end portion of the bore 53 which is located on the projector 100 side (+Z side). The bottom surface of the movable carriage 61 may be formed into a shape which can be fitted on the rail 55. Engaging the movable carriage 61 with the rail 55 can make the rail 55 less noticeable when externally viewing the gantry 11 while the movable carriage 61 is arranged on an end portion of the bore 53. The movable carriage 61 supports the screen 63 and the support arm 65. The movable carriage 61 is formed from a nonmagnetic material such as a resin, which has no influence on a magnetic field.

According to the above description, the rail 55 is provided in the gantry housing 51. If, however, the table top 131 and the movable carriage 61 can move along the central axis Z of the bore 53 without the rail 55, the rail 55 need not be provided in the gantry housing 51. For example, the rail 55 is not required for the couch of an apparatus other than a magnetic resonance imaging apparatus, such as an X-ray computed tomography apparatus, PET apparatus, or SPECT apparatus.

As shown in FIG. 5, connecting portions 69 to be connected to the table top 131 are formed on the movable carriage 61. As shown in FIG. 8, the connecting portions 69 connect the movable carriage 61 to the table top 131. A patient fixture 137 is attached to a front portion (+Z-axis direction side) of the table top 131. The patient fixture 137 fixes the head region of the patient P placed on the table top 131. The patient fixture 137 has a curved shape so as to cover the back of the head of the patient P without blocking the vision of the patient P placed on his/her back on the table top 131. That is, the frontal side of the head of the patient fixture 137 is open. Therefore, the patient fixture 137 can reduce the feeling of confinement felt by the patient P and also reduce the narrowing of the vision of the patient P. The patient fixture 137 is integrally molded from a nonmagnetic material such as a resin by using a mold having the above shape.

As shown in FIGS. 5, 6, 7, and 8, the screen 63 stands on the movable carriage 61. An image from the projector 100 (not shown) is projected on the screen 63. The screen 63 is provided so as to be tiltable with respect to the movable carriage 61. More specifically, the screen 63 is provided so as to be tilted by a tilting mechanism (not shown) provided on the movable carriage 61. Adjusting the tilt angle of the screen 63 with respect to the surface of the movable carriage 61 will hold the screen 63 perpendicular to or at a predetermined tilt angle with respect to the surface of the movable carriage 61. As described above, the projector 100 is arranged on the side opposite to the couch 13 with the screen 63 sandwiched in between them. In this case, the surface of the screen 63 which is located on the projector 100 side will be referred to as the reverse surface, and the surface of the screen 63 which is located on the couch 13 side will be referred to as the obverse surface. In order to project an image on the obverse surface, the screen 63 is preferably formed from a translucent material. As such a translucent material, a translucent plastic material, frosted glass material, or the like is preferably used. When the screen 63 is formed from a translucent material, the reverse surface of the screen is irradiated with projection light emerging from the projector 100, and an image corresponding to the projection light is projected on the obverse surface. This allows the patient P or the like to see the image projected on the obverse surface from the couch 13 side. The screen 63 may be of a type having a planar shape or a type having a curved shape. When having a curved shape, the screen is preferably arranged such that the concave surface faces the couch 13, that is, the concave surface forms an obverse surface. When the concave surface faces the couch 13, a portion around the back of the head region of the patient P placed on the table top 131 can be covered by the screen 63. This makes it possible to fill the visual field of the patient P with an image projected on the screen 63 and immerse the visual field in the image.

FIG. 9 is a schematic front view of the screen 63 arranged in the bore 53. As shown in FIG. 9, the screen 63 has an outer diameter RS smaller than a diameter RS of the inner wall 57 in contact with the bore 53 of the gantry housing 51. Designing the movable screen apparatus 15 to have the outer diameter RS smaller than the inner diameter RB allows the movable screen apparatus 15 to be inserted into the bore 53. Note that air is blown from a ventilation fan (not shown) provided on the gantry 11 into the bore 53. Providing a gap G1 between the edge of the screen 63 and the inner wall 57 can prevent air sent from the ventilation fan from being blocked by the screen 63. The outer diameter RS is preferably designed to be smaller than the inner diameter RB by 10 mm to 50 mm. In other words, the gap 61 is preferably designed to be 10 mm to 50 mm.

As shown in FIGS. 5, 6, 7, and 8, the support arm 65 is attached to the movable carriage 61. As described later, the support arm 65 is attached to the movable carriage 61 so as to be slidable in the Z-axis direction. The support arm 65 supports the reflecting plate 67 so as to arrange it in a space on the obverse surface side of the screen 63. The reflecting plate 67 is supported by the support arm 65 at a distance from the surface of the movable carriage 61 so as to avoid the reflecting plate 67 from coming into contact with the head region of the patient P placed on the table top 131 while the movable carriage 61 is connected to the table top 131. The support arm 65 has a shape so as not to block the vision of an external observer when he/she sees the screen 63 from the outside of the gantry 11. In order to prevent the support arm 65 from blocking the vision of the external observer, the support arm 65 preferably has a semi-annular shape or semi-saddle shape having an arcuated portion along the contour of the screen 63, as shown in FIGS. 5, 6, 7, and 8. In this case, the support arm 65 is attached to the movable carriage 61 such that the two ends of the support arm 65 are attached to side portions of the movable carriage 61, and the arcuated portion of the support arm 65 is located in a space on the obverse surface side of the screen 63. Note that the shape of the support arm 65 is not limited to the above semi-annular shape or semi-saddle shape, and may have any shape which allows the reflecting plate 67 to be arranged in the space on the obverse surface side of the screen 63. For example, the support arm 65 may be formed from a pair of arms each having an almost rod-like shape. In this case, one end of each of the pair of arms is preferably attached to a corresponding one of the two side portions of the movable carriage 61, and the other end of each of the pair of arms is preferably attached to the reflecting plate 67.

As shown in FIGS. 5, 6, 7, and 8, the reflecting plate 67 is provided on an almost uppermost portion of the support arm 65. The reflecting plate 67 reflects an image projected on the obverse surface of the screen 63. The reflecting plate 67 is formed from a nonmagnetic material and may be formed from any material which can optically reflect a target. For example, as the reflecting plate 67, it is possible to use a mirror obtained by depositing aluminum on an acrylic plate, a half mirror to which a dielectric film adheres, or the like. The patient P whose head region is placed on the patient fixture 137 can see an image projected on the obverse surface via the reflecting plate 67.

The reflecting plate 67 is rotatably provided on the support arm 65 to allow the patient P to manually adjust the angle of the reflecting plate 67. More specifically, a rotating mechanism (not shown) provided on the support arm 65 allows the patient P to rotate the reflecting plate 67 around a rotating shaft RR1. For example, the rotating shaft RR1 is provided parallel to the X-axis so as to make it possible to adjust the direction of the reflecting plate 67 with respect to the obverse surface of the screen 63. More specifically, the support arm 65 is preferably provided so as to make it possible to switch between the first angle for the first projection mode and the second angle for the second projection mode (which will be described later). The first projection mode is a mode of seeing an image on the screen 63 from the outside of the gantry 11 without via the reflecting plate 67. For this reason, the first angle of the reflecting plate 67 in the first projection mode is preferably set to an angle at which the reflecting plate 67 does not block the vision of the patient P or the like located outside the gantry 11, for example, almost the horizontal angle. The second projection mode is a mode of seeing an image inside the bore 53 via the reflecting plate 67. For this reason, the second angle of the reflecting plate in the second projection mode is preferably set to an arbitrary angle between the horizontal angle and the vertical angle in accordance with the physique and the like of the patient P as an observer.

In order to adjust the position of the reflecting plate 67 with respect to the Z-axis, the movable carriage 61 is preferably provided with a slide structure 71 of the support arm 65. FIG. 10 shows a side surface of the movable screen apparatus 15 with the support arm 65 in FIG. 6 being slid with respect to the Z-axis. As shown in FIGS. 6 and 10, the slide structure 71 has guides 611 formed on the movable carriage 61 to guide a slide along the Z-axis of the support arm 65. The guides 611 are provided on the two side surfaces of the movable carriage 61 along the Z-axis to avoid contact with the support arm 65 and the screen 63. The guides 611 may be implemented in any form. For example, the guides are implemented by gaps on the side surfaces of the movable carriage 61 along the Z-axis. As shown in FIGS. 6 and 10, in order to improve the slidability of the support arm 65, wheels 651 may be provided on base portions of the support arm 65 which face the guides 611. Providing the slide structure 71 allows a healthcare worker such as a doctor, technician, or nurse, the patient P, and the like to move the reflecting plate 67 toward or away from the screen 63 by pushing or pulling the support arm 65 in the Z-axis direction. This makes it possible to adjust the position of the reflecting plate 67 in the Z-axis direction.

According to the above description, the slide structure 71 is implemented by the guides 611 provided on the movable carriage 61 and the wheels 651 provided on the support arm 65. However, this embodiment is not limited to this. As the slide structure 71 according to this embodiment, it is possible to use any mechanism which can slide the support arm 65 relative to the movable carriage 61. For example, guides may be provided on the support arm 65 along the Z-axis, and wheels which run on the guides may be provided on the movable carriage 61. In addition, the slide structure 71 may be implemented by ball screws, slide rails, and the like.

FIG. 11 is a schematic side view of the movable screen apparatus 15 arranged in the bore 53 of the gantry 11. As shown in FIG. 11, the movable carriage 61 of the movable screen apparatus 15 is slidably provided on the rail 55. Typically, no driving apparatus is mounted on the movable screen apparatus 15. The movable screen apparatus 15 slides as the couch driving apparatus 135 slides the table top 131. Note that the patient P, healthcare worker, or the like can slide the movable screen apparatus 15 by pushing or pulling it with respect to the Z-axis.

The connection between the movable screen apparatus 15 and the table top 131 will be described next. FIG. 12 is a schematic side view of the movable screen apparatus 15 and the table top 131. Note that in FIG. 12, an illustration of the base 133 of the couch 13 is omitted. As shown in FIG. 12, the male connecting portions 69 are provided on the end portion of the movable carriage 61 of the movable screen apparatus 15 which is located on the couch side, and female connecting portions 139 corresponding to the male connecting portions 69 are provided in the end portion of the table top 131 which is located on the gantry housing 51 side. The male connecting portions 69 and the female connecting portions 139 have shapes that allow them to fit to each other. Fitting the male connecting portions 69 in the female connecting portions 139 will mechanically connect the movable screen apparatus 15 to the table top 131. More specifically, each male connecting portion 69 is implemented by at least one hook, and each female connecting portion 139 is implemented by at least one groove formed in the upper surface of the table top 131. The hook 69 is provided on the movable carriage 61 so as to pivot around a pivot shaft RR2. More specifically, the proximal end portion of the hook 69 is pivotally provided on the movable carriage 61 such that the distal end portion of the hook 69 protrudes from the movable carriage 61. Note that the hook 69 is preferably pivotally provided on the movable carriage 61 through a spring (not shown) to generate a restoring force downward (-Y-axis direction).

Figure 13:
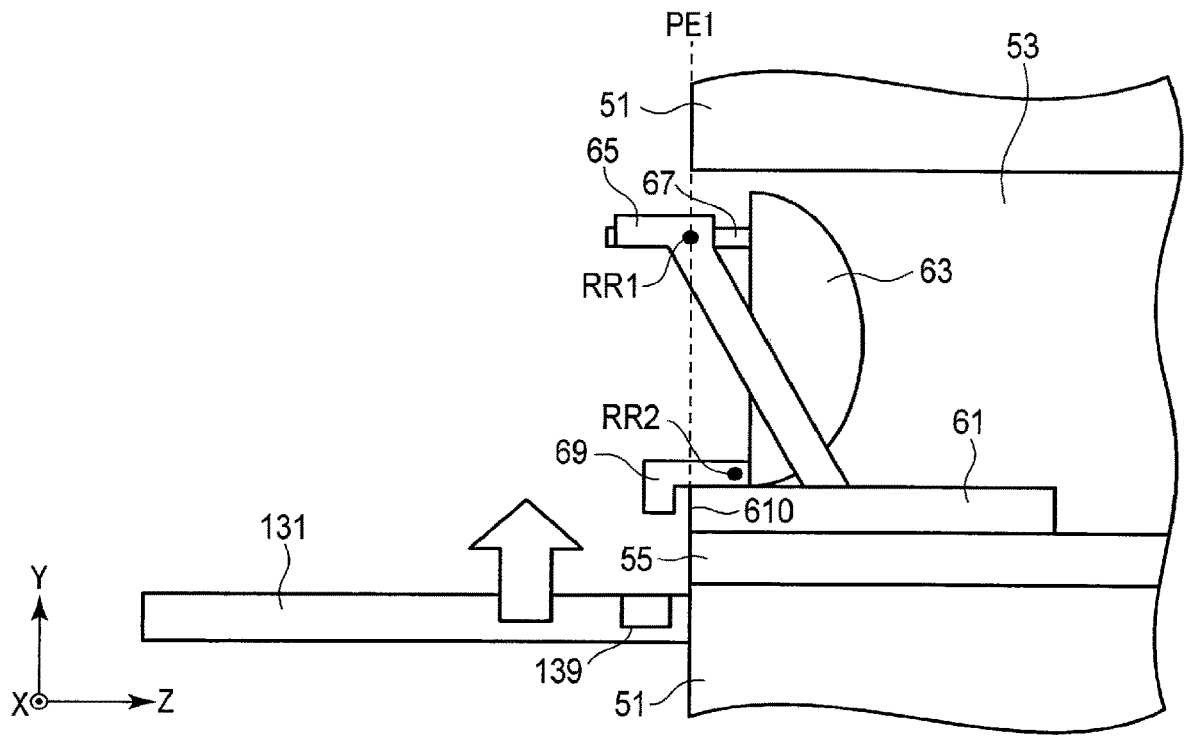
FIG. 13 is a view showing how the movable screen apparatus is connected to the table top according to this embodiment.

FIG. 13 shows the connection between the movable screen apparatus 15 and the table top 131. Typically, the movable screen apparatus 15 is connected to the table top 131 when the patient P is placed on the table top 131 and the table top 131 is inserted into the bore 53. As shown in FIG. 13, to connect the movable screen apparatus 15 to the table top 131, the movable screen apparatus 15 is arranged such that an end face 610 of the movable carriage 61 which is on the couch 13 side is located on a couch side end PE1 of the bore 53, and the distal end portion of the hook 69 protrudes from the couch side end PE1. Note that if the distal end portion of the hook 69 protrudes from the couch side end PE1, the end face 610 of the movable carriage 61 need not strictly match the couch side end PE1 and may be arranged nearer to the couch than the couch side end PE1 or inside the bore 53.

First of all, as shown in FIG. 13, the table top 131 is moved to locate the distal end portion of each hook 69 immediately above the corresponding groove 139 of the table top 131. Moving the table top 131 upward will fit the hook 69 in the groove 139. This can connect the movable screen apparatus 15 to the table top 131. Sliding the table top 131 by using the motive force of the couch driving apparatus 135 in the connected state makes it possible to slide the movable screen apparatus 15 having no self power source in conjunction with sliding of the table top 131. Note that, for example, the couch driving apparatus 135 moves the table top 131 in accordance with an instruction from the user via the input circuitry 36. As described above, according to this embodiment, it is possible to connect the table top 131 to the movable screen apparatus 15 by a simple operation of moving up the table top 131. Note that moving up the table top 131 is an operation for inserting the patient P into the bore 53 to perform MR imaging. That is, it is possible to connect the table top 131 to the movable screen apparatus 15 without providing any additional step.

Note that a mechanical error or the like of the couch 13 sometimes causes a positional shift between each groove 139 and the corresponding hook 69 in the Z-axis direction. In this case, even if the table top 131 is moved up, the groove 139 may not fit on the hook 69. In this case, the table top 131 may be moved up first and then slid toward the movable screen apparatus 15. As the hook 69 is pressed by sliding the table top 131, the table top 131 pushes away the hook 69 upward. The hook 69 pushed away upward generates a downward restoring force. This further slides the table top 131 so that the hook 69 can fit in the female connecting portion 139. According to this embodiment, even if the table top 131 cannot be connected to the movable screen apparatus 15 by being moved up, the table top 131 can be connected to the movable screen apparatus 15 by only being slid.

Figure 14:
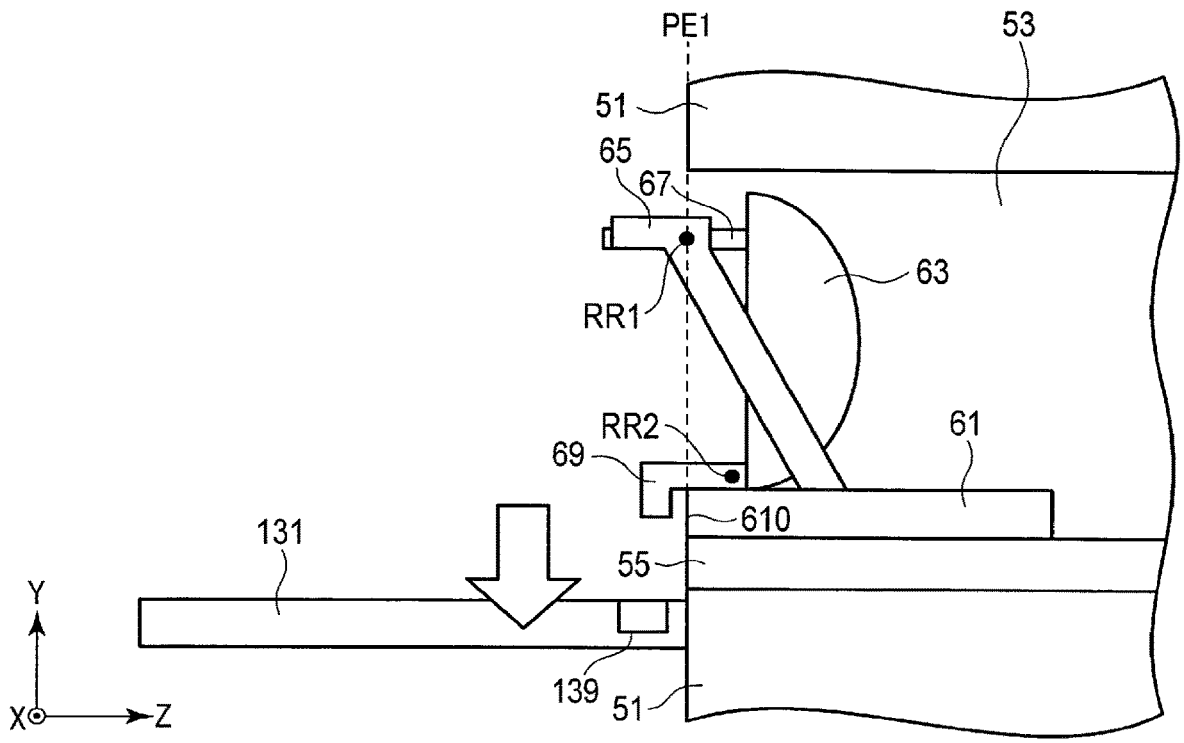
FIG. 14 is a view showing how the movable screen apparatus is disconnected from the table top according to this embodiment.

FIG. 14 shows the disconnection of between the movable screen apparatus 15 and the table top 131. As shown in FIG. 14, when the movable screen apparatus 15 is to be disconnected from the table top 131, the table top 131 is slid to the outside of the bore 53 so as to locate the end face 610 of the movable carriage 61 at the couch side end PE1. The table top 131 is then moved down. Each hook 69 is fixed in the horizontal direction (Z-axis direction and X-axis direction) with respect to the corresponding groove 139 but is not fixed in the vertical direction (Y-axis direction). Therefore, moving down the table top 131 can simply disconnect the movable screen apparatus 15 from the table top 131.

Note that the form of connection between the table top 131 and the movable screen apparatus 15 is not limited to the above form. The table top 131 and the movable screen apparatus 15 may be connected to each other by any form as long as they are connected to each other by moving up the table top 131, and are disconnected from each other by moving down the table top 131. Alternatively, a lock mechanism which can be manually or mechanically turned on and off may be provided to connect the table top 131 to the movable screen apparatus 15.

An example of the operation of the magnetic resonance imaging system according to this embodiment will be described next. FIG. 15 is a flowchart showing a typical procedure for an MR examination using the magnetic resonance imaging system according to the embodiment.

As shown in FIG. 15, first of all, before the patient P enters the examination room, a healthcare worker or the like arranges the movable screen apparatus 15 at the couch side end PE1 of the bore 53 (step S1). Arranging the movable screen apparatus 15 at the couch side end PE1 of the bore 53 can prevent the bore 53 from entering the vision of the patient P when he/she sees the gantry 11 from the outside of the gantry 11.

After step S1, the projector controller 200 controls the projector 100 so as to project a predetermined image on the movable screen apparatus 15 (a first projection mode P1). The mode of projecting an image on the movable screen apparatus 15 while the movable screen apparatus 15 is arranged at the couch side end PE1 of the bore 53 will be referred to as the first projection mode P1. To project an image by using the projector 100, first of all, a healthcare worker inputs a projection instruction via the input circuitry of the projector controller 200. Upon receiving the projection instruction, the projector controller 200 transmits the image data of the predetermined image to the projector 100. Upon receiving the image data, the projector 100 projects an image corresponding to the received image data onto the screen 63 of the movable screen apparatus 15. The image may be a moving image or still image. The contents of the image are not specifically limited. For example, the image may a moving image or still image having a relaxing effect, examination support information such as cautions to be observed at the time of an examination and the time until the end of the examination, or the like.

When the projection of the image in the first projection mode P1 starts, the patient P enters the examination room (step S2).

FIG. 16 shows the movable screen apparatus 15 in the first projection mode P1 when viewed from the gantry 11 side. FIG. 17 shows the movable screen apparatus 15 in the first projection mode P1 when viewed from the front surface of the gantry 11. As shown in FIGS. 16 and 17, the movable screen apparatus 15 in the first projection mode P1 is arranged such that the end face 610 of the movable carriage 61 is located at the couch side end PE1 of the bore 53. This arranges the screen 63 at or near the couch side end PE1 of the bore 53 (to be referred to as the couch side end portion hereinafter). Note that the couch side end portion at which the screen 63 is arranged in the first projection mode P1 may be arranged inside the bore 53 relative to the couch side end PE1 of the bore 53 or outside the bore 53 as long as the patient is not conscious of the inside of the bore 53 when seeing the screen 63 from the outside of the bore 53. Arranging the screen 63 at the couch side end portion can prevent the patient P from seeing the inside of the bore 53 because the screen 63 closes the bore 53. In addition, at this time, since an image PI is projected on the screen 63, it blunts the patient P's recognition that the bore 53 is an examination space and can reduce the feeling of fear of entrance into the bore 53.

In the first projection mode P1, to improve the visibility of the screen 63 from the outside of the gantry 11, the reflecting plate 67 is preferably held at an angle at which the reflecting plate 67 does not block the vision of the patient P or the like. For example, as described above, the angle of the reflecting plate 67 around the rotating shaft RR1 is preferably maintained at an almost horizontal angle by the support arm 65. Note that the angle of the reflecting plate 67 in the first projection mode P1 is not limited to an almost horizontal angle and may be decided at an arbitrary angle in accordance with the physique and the like of the patient P.

When the patient P sees an image projected on the movable screen apparatus 15 upon execution of step S2, the patient P is placed on the table top (step S3). In step S3, the head region of the patient P is fixed by the patient fixture 137 of the table top 131.

Upon execution of step S3, the table top 131 is moved up to connect the table top 131 to the movable screen apparatus 15 (step S4). More specifically, in step S4, the healthcare worker presses an up button provided on the gantry 11 or the couch 13. In response to the pressing of the up button, the imaging control circuitry 31 supplies an electrical signal (to be referred to as an up signal hereinafter) corresponding to the moving up of the table top 131 to the couch driving apparatus 135. Upon receiving the up signal, the couch driving apparatus 135 moves up the table top 131 in the Y-axis direction. When the table top 131 is moved up, the grooves 139 of the table top 131 are fitted on the hooks 69 of the movable screen apparatus 15 to connect the table top 131 to the movable screen apparatus 15. The mode of projecting an image on the movable screen apparatus 15 while the movable screen apparatus 15 is connected to the table top 131 will be referred to as a second projection mode P2.

Upon execution of step S4, projection by the first projection mode P1 is terminated. Note that the projection of an image by the first projection mode P1 need not always be terminated after the connection (step S4) between the table top 131 and the movable screen apparatus 15. For example, the projection of an image by the first projection mode P1 may be terminated in the interval between the instant the patient P is placed on the table top 131 and the instant the table top 131 is connected to the movable screen apparatus 15. Note that the projector 100 terminates the projection of an image upon receiving a projection stop signal supplied from the projector controller 200. The projector controller 200 supplies the projection stop signal to the projector 100 upon receiving an image stop instruction supplied from the healthcare worker via the input circuitry or the like.

Upon execution of step S4, the projector controller 200 controls the projector 100 so as to project a predetermined image on the movable screen apparatus 15 (second projection mode P2). More specifically, the healthcare worker inputs a projection instruction via the input circuitry of the projector controller 200. Upon receiving the projection instruction, the projector controller 200 transmits the image data of the predetermined image to the projector 100. Upon receiving the image data, the projector 100 projects the image corresponding to the received imaged data on the movable screen apparatus 15. The image may be identical to or different from the image projected in the first projection mode P1.

When the projection of an image by the second projection mode P2 starts, the table top 131 is inserted into the bore 53 (step S5). In step S5, the healthcare worker presses an insertion button provided on the gantry 11 or the couch 13. In response to the pressing of the insertion button, the imaging control circuitry 31 supplies an electrical signal (to be referred to as an insertion signal hereinafter) corresponding to the insertion of the table top 131 to the couch driving apparatus 135. Upon receiving the insertion signal, the couch driving apparatus 135 slides the table top 131 in the +Z-axis direction. Since the table top 131 is connected to the movable screen apparatus 15, the movable screen apparatus 15 also slides in the +Z direction in conjunction with the sliding of the table top 131. When the table top 131 slides to an imaging position, the healthcare worker finishes pressing the insertion button to stop the table top.

FIG. 18 shows the movable screen apparatus 15 in the second projection mode P2 when viewed from the gantry 11 side. As shown in FIG. 18, the patient P placed on the table top 131 in the second projection mode P2 can see an image projected on the obverse surface of the screen 63 via the reflecting plate 67. Since the table top 131 is connected to the movable screen apparatus 15, the distance between the patient P and the screen 63 is kept constant regardless of the sliding of the movable screen apparatus 15 in the Z-axis direction. This can increase the feeling of being immersed in an image projected on the screen 63 and reduce the feeling of confinement in the bore 53. The projection of an image by the second projection mode P2 is continued from the end of step S4 to the end of step S7.

Upon execution of step S5, MR imaging is performed (step S6). In step S6, the healthcare worker presses a start button for MR imaging. When the healthcare worker presses the start button, the imaging control circuitry 31 executes MR imaging by synchronously controlling the gradient field power supply 21, the transmission circuitry 23, and the reception circuitry 25 in accordance with a preset imaging sequence. The reception circuitry 25 acquires MR signals concerning the patient P by MR imaging. The reconstruction circuitry 32 then reconstructs MR images based on the MR signals. During MR imaging, the patient P can appreciate an image projected on the screen 63 via the reflecting plate 67. This allows the patient P to comfortably spend a relatively long time of MR imaging in the bore 53.

When MR imaging is completed upon execution of step S6, the table top 131 is retreated from the bore 53 (step S7). In step S7, the healthcare worker presses a retreat button provided on the gantry 11 or the couch 13. In response to the pressing of the retreat button, the imaging control circuitry 31 supplies an electrical signal (to be referred to as a retreat signal hereinafter) corresponding to the retreat of the table top 131 to the couch driving apparatus 135. Upon receiving the retreat signal, the couch driving apparatus 135 slides the table top 131 in the −Z-axis direction. When the table top 131 is slid out of the gantry 11, the movable screen apparatus 15 is arranged at the couch side end PE1 of the bore 53. Even while the table top 131 is moved out of the bore 53, the patient P can keep appreciating an image projected on the screen 63 via the reflecting plate 67.

Upon execution of step S7, the projection of an image in the second projection mode P2 is terminated. For example, the healthcare worker inputs a projection stop instruction via the input circuitry of the projector controller 200. Upon receiving the projection stop instruction, the projector controller 200 supplies a stop signal to the projector 100. Upon receiving the stop signal, the projector 100 terminates the projection of the image.

Upon execution of step S7, the table top 131 is moved down to disconnect the table top 131 from the movable screen apparatus 15 (step S8). More specifically, in step S8, the healthcare worker presses a down button provided on the gantry 11 or the couch 13. In response to the pressing of the down button, the imaging control circuitry 31 supplies an electrical signal (to be referred to as a down signal hereinafter) corresponding to the moving down of the table top 131 to the couch driving apparatus 135. Upon receiving the down signal, the couch driving apparatus 135 moves down the table top 131 in the Y-axis direction. When the table top 131 is moved down, the hooks 69 of the movable screen apparatus 15 come off the grooves 139 of the table top 131 to disconnect the table top 131 from the movable screen apparatus 15. When the table top 131 is moved down to an initial position, the healthcare worker stops pressing the down button.

Subsequently, the patient P gets down from the table top 131 and leaves the examination room.

This is the end of the description of an example of the operation of the magnetic resonance imaging system 1 according to this embodiment.

Note that the above example of the procedure for the MR examination is not limited to the above procedure for the example of the operation of the magnetic resonance imaging system 1 according to this embodiment. For example, in the above procedure, the up button and the insertion button are individually pressed to move the table top 131 from the initial position to the imaging position in the bore 53. However, this embodiment is not limited to this. For example, an automatic insertion button which collectively gives instructions to move up and insert the table top 131 may be pressed. In addition, in the above procedure, the retreat button and the down button are individually pressed to move the table top 131 from the inside of the bore 53 to the initial position. However, this embodiment is not limited to this. For example, an automatic retreat button which collectively gives instructions to retreat and move down the table top 131 may be pressed.

As described above, the medical image diagnostic apparatus 10 according to this embodiment includes the gantry 11, the couch 13, and the movable screen apparatus 15. The gantry 11 has the bore 53 and includes a medical imaging mechanism. The couch 13 moves the table top 131 along the central axis Z of the bore 53. In addition, the movable screen apparatus 15 is provided in the bore 53. The movable screen apparatus 15 includes the movable carriage 61, the screen 63, the reflecting plate 67, and the support arm 65. The movable carriage 61 is provided independently of the table top 131 so as to be movable along the central axis Z of the bore 53. The screen 63 is provided on the movable carriage 61, and an image from the projector 100 is projected on the screen 63. The reflecting plate 67 reflects an image projected on the screen 63. The support arm 65 is provided on the movable carriage 61 and supports the reflecting plate 67.

With the above arrangement, the medical image diagnostic apparatus 10 according to this embodiment can implement the first projection mode of projecting an image on the movable screen apparatus 15 while the movable screen apparatus 15 is arranged at the couch side end PE1 of the bore 53 and the second projection mode of projecting an image on the movable screen apparatus 15 while the table top 131 is connected to the movable screen apparatus 15. An image is projected in the first projection mode before the patient P is placed on the table top 131. In the first projection mode, an image can be projected on the screen 63 while the bore 53 is closed by the screen 63. The patient P located outside the bore 53 can see an image projected on the screen 63 without visually recognizing the inside of the bore 53. In the second projection mode, an image is projected while the patient P is placed on the table top 131 and the table top 131 is connected to the movable screen apparatus 15. Typically, an image is projected when the patient P placed on the table top 131 is inserted into the bore 53 to perform MR imaging.

As described above, the movable screen apparatus 15 includes the screen 63 and the reflecting plate 67, and the screen 63 is arranged behind the head region of the patient P, while the reflecting plate which reflects an image projected on the screen 63 is arranged in front of the patient P. In the second projection mode, since the table top 131 is connected to the movable screen apparatus 15, the distance between the screen 63 and the reflecting plate 67 can be kept constant regardless of the movement of the table top 131. This makes it possible to always project an image having a constant size on the reflecting plate 67. In addition, according to this embodiment, the patient P need not wear a structure covering the head region of the patient P, e.g., a head coil or head mounted display, and hence can see an image in a wide vision without feeling a sense of confinement. In addition, there is no need to provide the movable screen apparatus 15 in accordance with an imaging region or coil shape as compared with a case in which the reflecting plate 67 is mounted on the head coil.

As described above, consecutively executing the first projection mode and the second projection mode can terminate MR imaging without letting the patient P visually recognize, even once, the inside of the bore 53 after entering the examination room. Therefore, the patient P does not become conscious of the bore 53, and hence can appreciate an image without feeling any sense of confinement as compared with seeing an image in the bore 53 upon visually recognizing the bore 53. In addition, in the first projection mode, since the screen 63 is arranged on the couch side end portion as the entrance of the bore 53 and an image is projected on the screen 63, the patient P can be made to become conscious of the bore 53 as an image projection space. This makes it possible to reduce the feeling of anxiety of the patient P when he/she is inserted into the bore 53 of the table top 131.

According to this embodiment, therefore, it is possible to improve the interior comfortability in the bore of the gantry 11.

Application Example 1

In the above embodiment, the support arm 65 is slidably supported by the slide structure. However, this embodiment is not limited to this. For example, the support arm 65 may be pivotably provided by a link.

FIG. 19 is a schematic view of the movable screen apparatus 15 according to Application Example 1. As shown in FIG. 19, the movable carriage 61 is provided with a link 73. The link 73 supports the support arm 65 so as to allow it to pivot along a pivot shaft RR3. The pivot shaft RR3 is preferably provided parallel to the X-axis so as to allow the support arm 65 to be tilted down toward the movable carriage 61 or moved up. This can tilt the support arm 65 down toward the movable carriage 61 in the first projection mode. Tilting the support arm 65 down can prevent the reflecting plate 67 and the support arm 65 from blocking the vision of the patient P. In addition, in the second projection mode, the support arm 65 can be moved up from the movable carriage 61. Moving up the support arm 65 allows the patient P placed on the table top 131 to see an image projected on the screen 63 via the reflecting plate 67.

Application Example 2

In the above embodiment, the support arm 65 is supported by the slide structure and the link. However, this embodiment is not limited to this. For example, the support arm 65 may be supported by both the slide structure and the link.

FIG. 20 is a schematic view of the movable screen apparatus 15 according to Application Example 2. As shown in FIG. 20, the support arm 65 is supported by both the first link 73 and the slide structure 71. For example, the support arm 65 is preferably supported by the first link 73 so as to pivot around the pivot shaft RR3, and the first link 73 is preferably supported on the movable carriage 61 by the slide structure 71 so as to slide with respect to the Z-axis. In addition, the support arm 65 is configured to be folded by a second link 75. In this case, the support arm 65 includes a first arm 653, with the reflecting plate 67 being provided to be rotatable around the rotating shaft RR1, and a second arm 655 connected to the movable carriage 61 through the first link 73. The first arm 653 and the second arm 655 are connected to each other through the second link 75 so as to pivot around a second pivot shaft RR4. In this manner, the support arm 65 is configured to be folded by the second link 75. The support arm 65 is equipped with the second link 75 to make it possible to compactly house the support arm 65 and improve the degree of freedom in positioning the reflecting plate 67.

In addition, combining another slide structure or link with the above arrangement can further compactly house the support arm 65 and improve the degree of freedom in positioning the reflecting plate 67. This can further increase the degree of freedom of movement of the support arm 65.

Application Example 3

FIG. 21 is a side view of the movable screen apparatus 15 according to Application Example 3. FIG. 22 is an overall side view of the movable screen apparatus 15 and the gantry 11 according to Application Example 3. As shown in FIGS. 21 and 22, the movable screen apparatus 15 according to Application Example 3 is provided with an optical camera 80 for obtaining an image of the patient P placed on the table top 131.

As shown in FIG. 22, the optical camera 80 includes an objective lens 81 and an optical fiber 83. The optical camera 80 is connected to a CCD (Charge-Connected Device). The objective lens 81 and the optical fiber 83 are formed from a nonmagnetic material. The objective lens 81 is provide on the reflecting plate 67 so as to face the face of the patient P placed on the table top 131. More specifically, the optical camera 80 is preferably provided on, for example, a side surface portion of the reflecting plate 67 so as not to enter the vision of the patient P seeing the reflecting plate 67. The objective lens 81 converges or diverges light from the patient P. The optical fiber 83 is an optical waveguide which guides light from the objective lens 81. The optical fiber 83 connects the objective lens 81 to a CCD 85 provided outside the gantry 11 to guide light from the objective lens 81 to a CCD 85. The optical fiber 83 may be attached to the rail 55 or the surface of the inner wall 57 of the gantry housing 51 or may be embedded in the rail 55 or the gantry housing 51. The CCD 85 includes a plurality of light-receiving elements which receive light from the optical fiber 83 and convert the light into electrical signals. The CCD 85 generates optical image data for depicting a face of the patient P based on electrical signals from the plurality of light-receiving elements.

Since the optical fiber 83 which connects the objective lens 81 to the CCD 85 has rigidity, the optical fiber 83 may be damaged as the movable screen apparatus 15 slides. In order to prevent this, for example, there may be provided a mechanism which can connect the objective lens 81 to the CCD 85 while the optical fiber 83 keeps a predetermined curvature regardless of sliding of the movable screen apparatus 15.

Optical image data is supplied to the console 27 via the communication circuitry 34. The display circuitry 35 displays an optical image corresponding to the supplied optical image data. A healthcare worker or the like can monitor the patient P during MR imaging by observing the optical image.

As described above, in this embodiment, the optical camera 80 is provided on the movable screen apparatus 15 arranged in the bore 53, and hence is provided at a position nearer to the patient P than a conventional monitoring camera provided outside the gantry 11. This makes it possible to, for example, obtain an image of a facial expression of the patient P in the gantry 11, and hence to accurately grasp the condition of the patient P during MR imaging.

Figure 23:
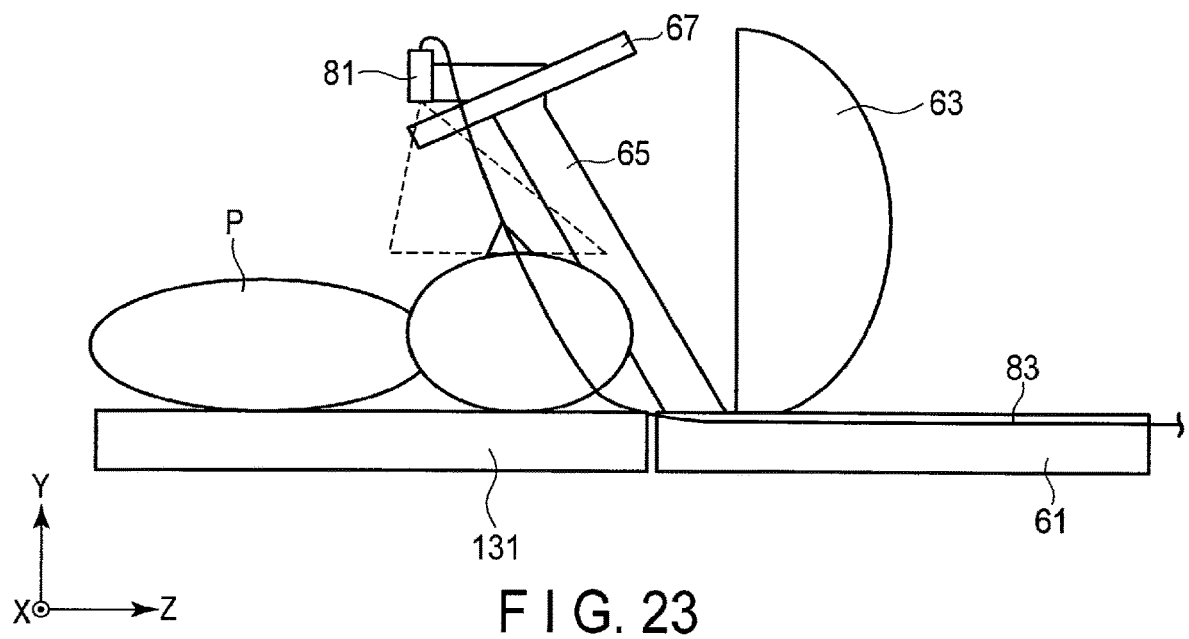
FIG. 23 is a view showing the movable screen apparatus with an optical camera being attached to a support arm according to Application Example 3.
Figure 24:
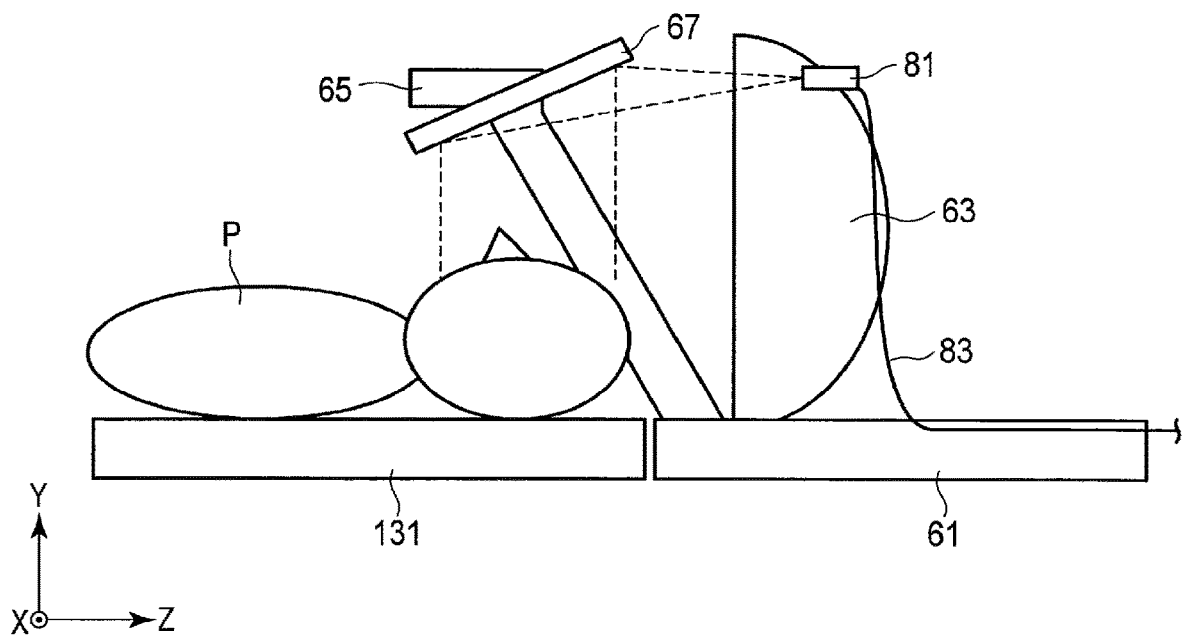
FIG. 24 is a view showing the movable screen apparatus with the optical camera being attached to the screen according to Application Example 3.

Although the optical camera 80, more specifically, the objective lens 81, is provided on the reflecting plate 67, this embodiment is not limited to this. The objective lens 81 may be provided on the support arm 65 as long as an image of the face of the patient P can be obtained, as shown in FIG. 23. In addition, the optical camera 80, more specifically, the objective lens 81, may be provided on the screen 63, as shown in FIG. 24. If the objective lens 81 is provided on the screen 63, it is difficult to make the objective lens 81 squarely face the head region of the patient P because of the positional relationship between the screen 63 and the head region of the patient P. For this reason, the objective lens 81 is preferably provided at an end portion of the screen 63 so as to project an image of the head region of the patient P via the reflecting plate 67.

Application Example 4

According to Application Example 3, the optical camera 80 is used to monitor the patient P. However, this embodiment is not limited to this. Assume that in Application Example 4, the optical camera 80 is used to acquire the body motion information of the patient P. In Application Example 4, it is also preferable that the optical camera 80 is provided on the reflecting plate 67, the screen 63, or the support arm 65 so as to obtain an image of a region of a body motion acquisition target. Note that body motion information is position information such as an arbitrary point which changes accompanying the body motion of the patient P. An optical image obtained by the optical camera 80 includes the position information of the above feature point which changes accompanying the body motion of the patient P.

In Application Example 4, the image processing circuitry 33 performs body motion correction for a reconstructed image by using an optical image obtained by the optical camera 80. For example, the image processing circuitry 33 tracks the position of a feature point of a time-series optical image in chronological order and calculates the movement amount of the feature point. As a feature point, it is possible to set an arbitrary region such as the chin, forehead, or cervical spine of the patient P or a marker attached to the patient P depicted in an optical image. The image processing circuitry 33 then generates an image having undergone body motion correction by coordinate-transforming the reconstructed image in accordance with the calculated movement amount.

Note that in Application Example, 4, the optical camera 80 acquires body motion information. However, this embodiment is not limited to this. For example, an optical sensor, ultrasonic sensor, or acceleration sensor may be used to acquire the body motion information of an arbitrary point on the patient P. In addition, the optical camera according to Application Example 4 may be provided independently of a monitoring camera for the patient P according to Application Example 3.

Application Example 5

The movable screen apparatus 15 according to Application Examples 5 and 6 has a vibrating membrane which transmits or receives or transmits and receives sounds. The vibrating membrane is incorporated in a microphone or loudspeaker which receives sounds. Application Example 5 will exemplify a case in which the vibrating membrane is incorporated in the microphone. Application Example 6 will exemplify a case in which the vibrating membrane is incorporated in the loudspeaker.

FIG. 25 is a side view of the movable screen apparatus 15 according to Application Example 5. FIG. 26 is an overall side view of the movable screen apparatus 15 and the gantry 11 according to Application Example 5.

As shown in FIGS. 25 and 26, the movable screen apparatus 15 according to Application Example 5 is provided with a microphone 91. The microphone 91 is provided to collect sounds generated from the patient P. For example, the microphone 91 is attached to the reflecting plate 67. The microphone 91 is connected to an amplifier 95 provided outside the bore 53 via a cable 93. The microphone 91 includes, for example, a vibrating plate and a converter, and converts the vibrations of the vibrating plate produced by sounds into electrical signals (audio signals). An audio signal is supplied to the converter via the cable and amplified by the converter. The audio signal amplified by the converter is transmitted to the console 27 wiredly or wirelessly. The transmitted audio signal is output as a sound via a loudspeaker or the like provided on the console 27. This makes it possible to transmit sounds from the patient P to a healthcare worker in the control room or the like.

The microphone 91 according to this embodiment can be of any type as long as it is nonmagnetic. However, as the microphone 91 according to the embodiment, for example, a highly sensitive, nonmagnetic optical microphone is suitably used.

In the above case, the microphone 91 is provided on the reflecting plate 67. However, the microphone 91 can be provided at any place as long as it can collect sounds from the patient P. For example, the microphone 91 may be provided on another structure of the movable screen apparatus 15, such as the support arm 65 or the screen 63.

In addition, the microphone 91 according to this embodiment is not limited to the purpose of collecting sounds from the patient P. For example, the microphone 91 according to the embodiment may be used for collecting drive sounds generated by the gantry 11 for the purpose of noise canceling.

Application Example 6

FIG. 27 is a side view of the movable screen apparatus 15 according to Application Example 6. As shown in FIG. 27, the movable screen apparatus 15 according to Application Example 6 is provided with a loudspeaker 97. More specifically, the loudspeaker 97 is preferably provided on the support arm 65 arranged near the head region of the patient P. The loudspeaker 97 generates sounds corresponding to various applications.

The loudspeaker 97 is connected to the projector controller 200 wiredly or wirelessly. In this case, the loudspeaker 97 preferably generates a sound transmitted from the projector controller 200, which corresponds to an image projected from the projector 100 onto the movable screen apparatus 15. Since a patient can see an image while listening to sounds, he/she can comfortably spend time in the bore 53.

In addition, the loudspeaker 97 may be connected to the console 27 wiredly or wirelessly. In this case, the loudspeaker 97 may output sounds from a healthcare worker which are collected by a microphone provided for the console 27. This makes it possible to transmit an instruction or the like from the healthcare worker to the patient P even during MR imaging.

Note that for communication with the patient P, the loudspeaker 97 according to Application Example 6 is preferably combined with the microphone 91 according to Application Example 5. For example, providing the loudspeaker 97 according to Application Example 6 and the microphone 91 according to Application Example 5 on the movable screen apparatus 15 allows the patient P and a healthcare worker to communicate with each other. In addition, when the patient P is a child, the patient P in the bore 53 can communicate with his/her parents in the control room. This can reduce the feeling of anxiety of the patient P, who is, for example, a child, in the bore 53.

In addition, for noise cancellation, the loudspeaker 97 according to Application Example 6 is preferably combined with the microphone 91 according to Application Example 5. In this case, the microphone 91 collects a drive sound from the gantry 11 and transmits an electrical signal corresponding to the drive sound to the console 27. The system control circuitry 38 calculates the opposite phase of the drive sound by analyzing the audio signal of the drive sound. The system control circuitry 38 then generates an audio signal (to be referred to as a cancel signal hereinafter) having a phase opposite to the drive sound. The communication circuitry 34 transmits the cancel signal to the loudspeaker 97. The loudspeaker 97 converts the transmitted cancel signal to an acoustic wave (to be referred to as a cancel sound hereinafter) and outputs it. Since the drive sound from the gantry 11 is opposite in phase to the cancel sound, the drive sound in a space around the head region of the patient P is canceled out by the cancel sound. In this embodiment, since the movable screen apparatus 15 provided in the gantry 11 is provided with the microphone 91 and the loudspeaker 97, it is possible to cancel out a drive sound propagating around the patient P more accurately. This can therefore reduce the feeling of discomfort of the patient P which is caused by a drive sound.

Application Example 7

The support arm 65 is located in front of (on the couch 13 side) the screen 63 in the first projection mode. For this reason, the support arm 65 may block the vision of the patient P when he/she located outside the gantry 11 sees an image on the screen 63. Part of projection light (to be referred to as surplus light hereinafter) emerging from the projector 100 in the second projection mode does not irradiate the screen 63 but irradiates a portion of the inner wall 57 located in front of the screen 63 through the gap between the gantry housing 51 and the inner wall 57. An image (to be referred to as a surplus image hereinafter) corresponding to surplus light is projected on the portion of the inner wall 57. However, a surplus image does not sometimes enter the vision of the patient P by being blocked by the support arm 65 depending on the positional relationship between the portion of the inner wall 57 and the head region of the patient P. In order to solve these problems, the support arm 65 is preferably formed to be transparent partly or entirely. This can prevent the support arm 65 from hindering visual recognition of an image projected on the screen 63 in the first projection mode and prevent the support arm 65 from hindering visual recognition of a surplus image projected on the portion of the inner wall 57 in the second projection mode.

Application Example 8

FIG. 28 is a view showing an X-Z section (horizontal section) of the support arm 65 according to this embodiment. Although FIG. 28 shows the table top 131 and the movable carriage 61 so as to clarify the positional relationship between them and the support arm 65, the support arm 65, the table top 131, and the movable carriage 61 are not actually located at the same height. As shown in FIG. 28, when a horizontal section of the support arm 65 has a rectangular shape, a surface 65A facing the patient P and perpendicular to the X-axis enters the vision of the patient P. In this case, a surface 65B facing the projector 100 of the support arm 65 and perpendicular to the Z-axis is irradiated with projection light, and the surface 65A of the support arm 65 is not irradiated with the projection light. This makes the patient P visually recognize the surface 65A as a dark surface.

FIG. 29 is a view showing an X-Z section (horizontal section) of a support arm 65' according to Application Example 8. Although FIG. 29 shows the table top 131 and the movable carriage 61 so as to clarify the positional relationship between them and the support arm 65', the support arm 65', the table top 131, and the movable carriage 61 are not actually located at the same height. As shown in FIG. 29, the support arm 65' according to Application Example 8 has a shape that can reflect projection light from the projector 100 toward an inside space RI1 surrounded by the support arm 65'. More specifically, the support arm 65' is preferably formed such that a surface 65'A of the support arm 65' which faces the projector 100 tilts toward the inside space RI1 with respect to the X-axis. For example, as shown in FIG. 29, the support arm 65' is preferably formed to have a horizontal section having a triangular shape. In this case, although the surface 65'A enters the vision of the patient P, since the surface 65'A tilts with respect to the X-axis, the surface 65'A can reflect projection light from the projector 100 toward the patient P. This allows the patient P to visually recognize a surplus image projected on the surface 65'A.

Application Example 9

In the above embodiment, the screen 63 is directly irradiated with projection light emerging from the projector 100.

However, the embodiment is not limited to this. For example, the following form is conceivable. The projector controller 200 is connected to one end (to be referred to as an entrance end hereinafter) of an optical fiber, and the other end (to be referred to as an exit end hereinafter) is connected to the nonmagnetic projector 100. The nonmagnetic projector 100 is attached to a portion of one of the movable carriage 61, the support arm 65, and the reflecting plate 67 included in the movable screen apparatus 15, which is located on the front side (couch 13 side) of the screen 63, so as to make the exit portion of the projector 100 face the screen 63. With the above arrangement, the obverse surface (the surface on the couch 13 side) of the screen 63 can be irradiated with projection light corresponding to image data transmitted from the projector controller 200 to the projector 100 via the optical fiber. This makes it possible to always project images on the screen 63 in a predetermined size.

Application Example 10

In the above embodiment, in the first projection mode, an image from the projector 100 is projected on the screen 63 of the movable screen apparatus 15 installed at the couch side end PE1 of the bore 53. However, this embodiment is not limited to this. For example, another screen may be arranged on a wall surface of the gantry housing 51 which is located on the couch 13 side so as to close the bore 53, and an image from the projector 100 may be projected on the screen. In this case, the movable screen apparatus 15 is preferably retreated out of the bore 53 so as not to block projection light from the projector 100. Alternatively, an image may be projected from the projector 100 onto the screen without retreating the movable screen apparatus 15 out of the bore 53. In addition, a target on which an image is to be projected in the first projection mode is not limited to a screen. For example, a spatial imaging apparatus may be used to project an image in a space at the couch side end PE1 of the bore 53 so as to close the bore 53.

The medical image diagnostic apparatus and the magnetic resonance imaging apparatus according to at least one of the embodiments described above can improve the interior comfortability in the bore of the gantry.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image diagnostic apparatus comprising:
a gantry including a bore and a mechanism for medical imaging;
a couch including a table top and a base, the base being configured to support the table top and move the table top relative to the gantry along a central axis of the bore and along a vertical direction;
a movable base which is structurally separated from the table top and connectable to the table top, and provided in the bore so as to move along the central axis of the bore;
a screen which is provided on the movable base and on which an image from a projector is projected;
a reflecting plate that reflects the image projected on the screen;
a support body provided on the movable base and that supports the reflecting plate; and
a connecting portion which connects between the table top and the movable base;
wherein the table top connects with the movable base by moving upward to a position to be connected and disconnects from the movable base by moving downward from the position to be connected, while at least a portion of the movable base is arranged inside the bore.

2. The apparatus of claim 1, wherein the movable base is arranged in the bore so as to position the screen at an end portion of the bore while the table top is arranged outside the bore.

3. The apparatus of claim 1, wherein the connecting portion includes a first connecting portion which is provided on the movable base and a second connecting portion which is provided on the table top to be connected to the first connecting portion.

4. The apparatus of claim 3, wherein the first connecting portion comprises a hook, and
the second connecting portion comprises a groove configured to be fitted on the hook.

5. The apparatus of claim 3, wherein the movable base moves horizontally along the central axis in the bore in conjunction with horizontal movement of the table top while the movable base is connected to the table top.

6. The apparatus of claim 3, wherein the first connecting portion comprises a pivot shaft and a hook configured to rotate about the pivot shaft, and
the second connecting portion comprises a groove configured to be fitted to the hook when the hook is rotated about the pivot shaft to a horizontal position.

7. The apparatus of claim 6, wherein the pivot shaft is above, in a vertical direction, an upper surface of the table top when the table top is in the position to be connected.

8. The apparatus of claim 1, wherein the support body supports the reflecting plate so as to switch an angle of the reflecting plate between a horizontal angle and a vertical angle.

9. The apparatus of claim 1, wherein the support body rotatably supports the reflecting plate at a position spaced apart from the movable base on an opposite side of the screen to the projector.

10. The apparatus of claim 1, wherein the movable base includes at least one of a slide structure configured to slide the support body so as to be configured to move the reflecting plate toward or away from the screen and a link configured to make the support body pivot around a predetermined pivot shaft so as to move the reflecting plate toward or away from the screen.

11. The apparatus of claim 1, wherein the movable base includes a wheel which rolls on a rail installed in the bore.

12. The apparatus of claim 1, wherein the support body has a foldable structure.

13. The apparatus of claim 1, wherein the movable base supports the screen at a vertical angle with respect to the movable base or a predetermined tilt angle with respect to a vertical angle.

14. The apparatus of claim 1, wherein the screen has an outer diameter smaller than an inner diameter of the bore by 10 mm to 50 mm.

15. The apparatus of claim 1, further comprising an imaging device provided on at least one of the screen, the reflecting plate, and the support body and configured to obtain an image of a person lying on the table top.

16. The apparatus of claim 15, wherein the imaging device comprises
an objective lens provided on at least one of the screen, the reflecting plate, and the support body,
an optical waveguide configured to guide light from the objective lens, and
a photodetector provided outside the bore and configured to receive light from the optical waveguide.

17. The apparatus of claim 1, further comprising a body motion information acquisition device that includes at least one of an optical camera, an optical sensor, an ultrasonic sensor, or an acceleration sensor, and is provided on at least one of the screen, the reflecting plate, and the support body and configured to acquire body motion information which changes in accordance with a motion of a person lying on the table top.

18. The apparatus of claim 1, further comprising a vibrating membrane provided on at least one of the screen, the reflecting plate, and the support body and configured to transmit or receive a sound or transmit and receive a sound.

19. The apparatus of claim 1, further comprising an image display device configured to project an image on an end portion of the bore on which the table top is arranged while the table top is arranged outside the bore.

20. The apparatus of claim 1, wherein the screen is located so as to close the bore when the table top moves downward to be disconnected from the movable base.

21. A medical image diagnostic apparatus comprising:
a gantry including a bore and a mechanism for medical imaging;
a couch including a table top and a base, the base being configured to support the table top and move the table top relative to the gantry along a central axis of the bore and along a vertical direction;
a movable base which is structurally separated from the table top and connectable to the table top, and provided in the bore so as to move along the central axis of the bore;
a screen which is provided on the movable base and on which an image from a projector is projected;
a reflecting plate that reflects the image projected on the screen;
a support body provided on the movable base and that supports the reflecting plate; and
a connecting portion which connects between the table top and the movable base;
wherein the table top connects with the movable base and disconnects from the movable base, while the movable base is arranged at a couch side end portion of the gantry.

22. The apparatus of claim 21, wherein the table top connects with the movable base and disconnects from the movable base, while the couch side end portion of the movable base is arranged at the couch side end portion of the gantry.

23. The apparatus of claim 21 wherein the apparatus is a magnetic resonance imaging apparatus.

* * * * *